(12) United States Patent
Snyder et al.

(10) Patent No.: US 8,399,383 B2
(45) Date of Patent: Mar. 19, 2013

(54) PROTEIN CHIPS FOR HIGH THROUGHPUT SCREENING OF PROTEIN ACTIVITY

(75) Inventors: Michael Snyder, Fairfield, CT (US); Mark Reed, Monroe, CT (US); Heng Zhu, New Haven, CT (US); James Frank Klemic, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/849,781

(22) Filed: May 4, 2001

(65) Prior Publication Data

US 2003/0207467 A1 Nov. 6, 2003

Related U.S. Application Data

(60) Provisional application No. 60/201,921, filed on May 4, 2000, provisional application No. 60/221,034, filed on Jul. 27, 2000.

(51) Int. Cl.
*C40B 40/02* (2006.01)
*C40B 40/10* (2006.01)

(52) U.S. Cl. ............. 506/14; 506/13; 436/86; 436/518; 436/527; 435/288.4

(58) Field of Classification Search ............... 435/6, 7.1, 435/7.5, 287.1, 288.3, 288.4, 287.9; 436/518, 436/524, 525, 527, 528, 86; 422/50, 55, 422/67, 82.05, 65; 506/14, 13
See application file for complete search history.

(56) References Cited

U.S. PATENT DOCUMENTS

| | | | |
|---|---|---|---|
| 4,071,409 A | 1/1978 | Messing et al. | |
| 4,281,061 A | 7/1981 | Zuk et al. | |
| 4,444,879 A * | 4/1984 | Foster et al. ................... | 422/56 |
| 4,483,929 A | 11/1984 | Szoka | |
| 4,514,508 A | 4/1985 | Hirschfeld | |
| 4,562,157 A | 12/1985 | Lowe et al. | |
| 4,591,570 A | 5/1986 | Chang | |
| 4,722,896 A | 2/1988 | Kadish et al. | |
| 4,728,591 A | 3/1988 | Clark et al. | |
| 4,802,951 A | 2/1989 | Clark et al. | |
| 4,816,567 A | 3/1989 | Cabilly et al. | |
| 4,894,146 A | 1/1990 | Giddings | |
| 4,987,032 A | 1/1991 | Miyasaka et al. | |
| 4,994,373 A | 2/1991 | Stavrianopoulos et al. | |
| 5,096,807 A | 3/1992 | Leaback et al. | |
| 5,143,854 A | 9/1992 | Pirrung et al. | |
| 5,154,808 A | 10/1992 | Miyasaka et al. | |
| 5,242,828 A | 9/1993 | Bergstrom et al. | |
| 5,252,743 A | 10/1993 | Barrett et al. | |
| 5,262,322 A | 11/1993 | Liu et al. | |
| 5,270,167 A | 12/1993 | Francoeur et al. | |
| 5,283,173 A | 2/1994 | Fields et al. | |
| 5,296,114 A | 3/1994 | Manz et al. | |
| 5,296,144 A | 3/1994 | Sternina et al. | |
| 5,304,487 A | 4/1994 | Wilding et al. | |
| 5,348,886 A | 9/1994 | Lee et al. | |
| 5,376,252 A | 12/1994 | Ekstrom et al. | |
| 5,384,261 A | 1/1995 | Winkler et al. | |
| 5,405,766 A | 4/1995 | Kallury et al. | |
| 5,405,783 A | 4/1995 | Pirrung et al. | |
| 5,412,087 A | 5/1995 | McGall et al. | |
| 5,424,186 A | 6/1995 | Fodor et al. | |
| 5,429,807 A | 7/1995 | Matson et al. | |
| 5,432,099 A | 7/1995 | Ekins | |
| 5,441,876 A | 8/1995 | Singh et al. | |
| 5,445,934 A | 8/1995 | Fodor et al. | |
| 5,466,589 A | 11/1995 | Olinger et al. | |
| 5,489,678 A | 2/1996 | Fodor et al. | |
| 5,498,545 A | 3/1996 | Vestal et al. | |
| 5,506,121 A | 4/1996 | Skerra et al. | |
| 5,510,270 A | 4/1996 | Fodor et al. | |
| 5,512,492 A | 4/1996 | Herron et al. | |
| 5,516,635 A | 5/1996 | Ekins et al. | |
| 5,532,128 A | 7/1996 | Eggers | |
| 5,532,142 A | 7/1996 | Johnston et al. | |
| 5,538,897 A | 7/1996 | Yates, III et al. | |
| 5,541,070 A | 7/1996 | Kauvar | |
| 5,545,531 A | 8/1996 | Rava et al. | |
| 5,580,733 A | 12/1996 | Levis et al. | |
| 5,585,069 A | 12/1996 | Zanzucchi et al. | |

(Continued)

FOREIGN PATENT DOCUMENTS

| EP | 0619321 | 12/1994 |
|---|---|---|
| EP | 0 818 467 | 1/1998 |

(Continued)

OTHER PUBLICATIONS

Hunter et al., "The protein kinases of budding yeast: six score and more", 1997, Trends in Biochemical Sciences, 22(1):18-22.*

Maskos et al., "Oligonucleotide hybridization on glass supports: a novel linker for oligonucleotide synthesis and hybridisation properties of oligonucleotides synthesisedin situ", 1992, Nucleic Acids Research, 20(7):1679-1684.*

Bielke et al., "Characterization of a novel murine testis-specific serine/threonine kinase", 1994, Gene, 139(2):235-239.*

Stern et al., "Spk1, a new kinase from *Saccharomyces cerevisiae*, phrosphorylates proteins on serine, threonine, and tyrosine" 1991, Molecular and Cellular Biology, 11(2):987-1001.*

Hanks et al., May 1995, FASEB, 9(8), pp. 576-596.*

(Continued)

*Primary Examiner* — Teresa Wessendorf
(74) *Attorney, Agent, or Firm* — Sterne, Kessler, Goldstein & Fox P.L.L.C.

(57) ABSTRACT

The present invention relates to protein chips useful for the large-scale study of protein function where the chip contains densely packed reaction wells. The invention also relates to methods of using protein chips to assay simultaneously the presence, amount, and/or function of proteins present in a protein sample or on one protein chip, or to assay the presence, relative specificity, and binding affinity of each probe in a mixture of probes for each of the proteins on the chip. The invention also relates to methods of using the protein chips for high density and small volume chemical reactions. Also, the invention relates to polymers useful as protein chip substrates and methods of making protein chips. The invention further relates to compounds useful for the derivatization of protein chip substrates.

28 Claims, 12 Drawing Sheets

U.S. PATENT DOCUMENTS

Figure 1A:
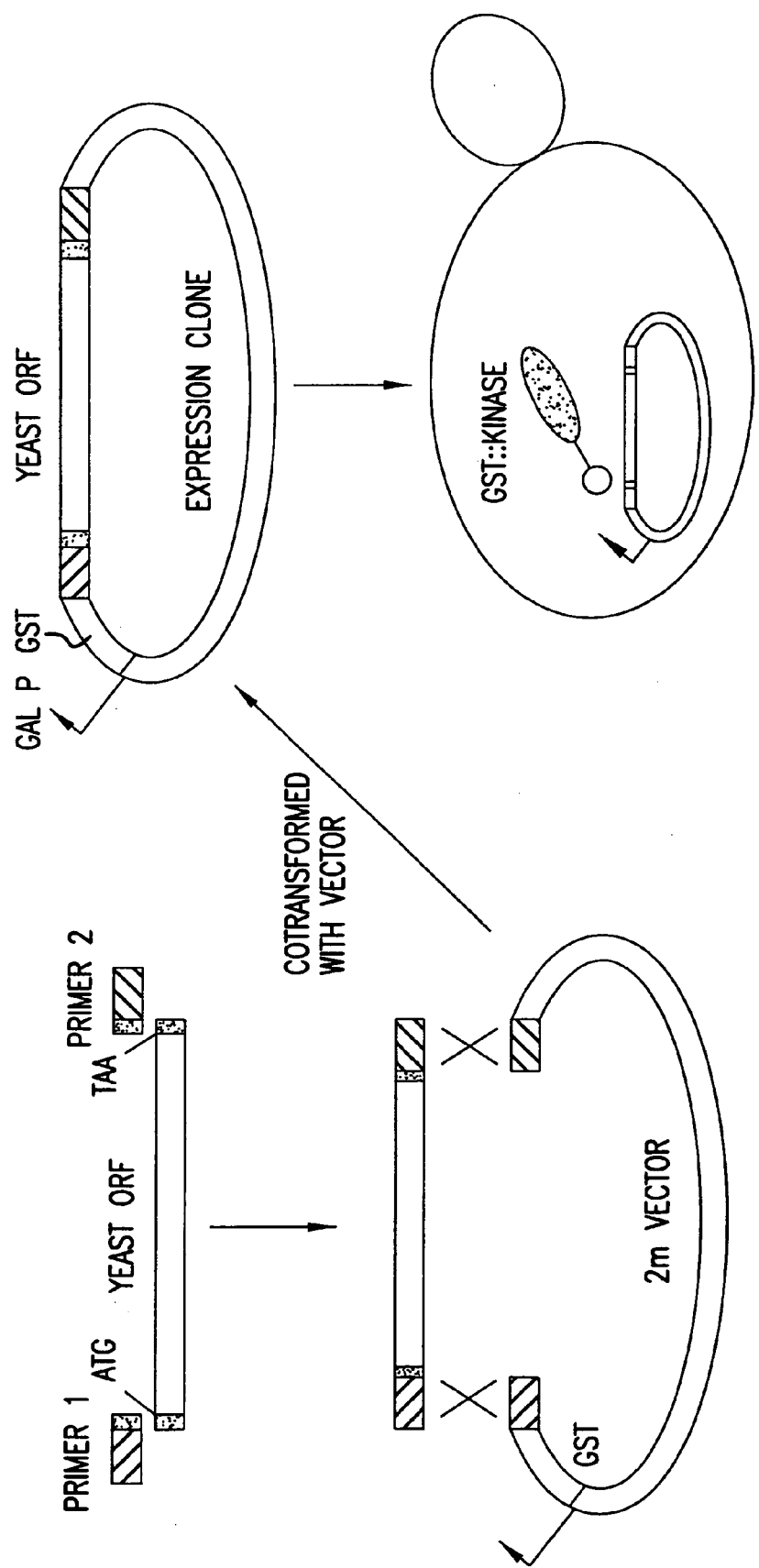

| | | | |
|---|---|---|---|
| 5,585,639 A | 12/1996 | Dorsel et al. ............... 250/458.1 | |
| 5,593,838 A | 1/1997 | Zanzucchi et al. | |
| 5,605,662 A | 2/1997 | Heller et al. | |
| 5,620,850 A | 4/1997 | Bamdad et al. | |
| 5,624,711 A | 4/1997 | Sundberg et al. | |
| 5,627,369 A | 5/1997 | Vestal et al. | |
| 5,629,213 A | 5/1997 | Kornguth et al. | |
| 5,637,469 A | 6/1997 | Wilding et al. | |
| 5,643,948 A | 7/1997 | Driedger et al. | |
| 5,653,939 A | 8/1997 | Hollis et al. ................... 422/50 | |
| 5,674,712 A | 10/1997 | Grandi et al. | |
| 5,677,195 A | 10/1997 | Winkler et al. | |
| 5,677,196 A | 10/1997 | Herron et al. | |
| 5,681,484 A | 10/1997 | Zanzucchi et al. | |
| 5,688,642 A | 11/1997 | Chrisey et al. | |
| 5,720,928 A | 2/1998 | Schwartz | |
| 5,726,026 A | 3/1998 | Wilding et al. | |
| 5,741,700 A | 4/1998 | Ershov et al. | |
| 5,744,305 A | 4/1998 | Fodor et al. | |
| 5,763,170 A | 6/1998 | Raybuck | |
| 5,766,908 A | 6/1998 | Klein et al. | |
| 5,776,674 A | 7/1998 | Ulmer | |
| 5,776,706 A | 7/1998 | Siiman et al. | |
| 5,776,748 A | 7/1998 | Singhvi et al. ................ 435/180 | |
| 5,807,522 A | 9/1998 | Brown et al. | |
| 5,807,755 A | 9/1998 | Ekins | |
| 5,821,063 A | 10/1998 | Patterson et al. | |
| 5,827,658 A | 10/1998 | Iiang | |
| 5,834,319 A | 11/1998 | Ekins | |
| 5,837,551 A | 11/1998 | Ekins | |
| 5,837,832 A | 11/1998 | Chee et al. | |
| 5,843,767 A | 12/1998 | Beattie ....................... 435/287.1 | |
| 5,846,819 A | 12/1998 | Pausch et al. | |
| 5,854,018 A | 12/1998 | Hitzeman et al. | |
| 5,858,188 A | 1/1999 | Soane et al. | |
| 5,858,804 A | 1/1999 | Zanzucchi et al. | |
| 5,861,242 A | 1/1999 | Chee et al. | |
| 5,861,254 A | 1/1999 | Schneider et al. | |
| 5,866,345 A | 2/1999 | Wilding et al. | |
| 5,866,362 A | 2/1999 | Cousens et al. | |
| 5,866,363 A | 2/1999 | Pieczenik | |
| 5,874,219 A | 2/1999 | Rava et al. | |
| 5,885,793 A | 3/1999 | Griffiths et al. | |
| 5,905,024 A | 5/1999 | Mirzabekov et al. | |
| 5,919,523 A | 7/1999 | Sundberg et al. | |
| 5,922,591 A | 7/1999 | Anderson et al. | |
| 5,922,617 A * | 7/1999 | Wang et al. ................... 204/406 | |
| 5,925,552 A | 7/1999 | Keogh et al. | |
| 5,942,443 A | 8/1999 | Parce et al. | |
| 5,945,334 A | 8/1999 | Besemer et al. | |
| 5,948,621 A | 9/1999 | Turner et al. | |
| 5,965,124 A | 10/1999 | Feinberg et al. | |
| 5,965,389 A | 10/1999 | Raymond et al. | |
| 5,981,734 A | 11/1999 | Mirzabekov et al. | |
| 6,001,607 A | 12/1999 | Tang et al. | |
| 6,040,193 A | 3/2000 | Winkler et al. | |
| 6,051,380 A | 4/2000 | Sosnowski et al. ................ 435/6 | |
| 6,061,476 A | 5/2000 | Nichani | |
| 6,064,754 A | 5/2000 | Parekh et al. | |
| 6,075,875 A | 6/2000 | Gu | |
| 6,083,763 A | 7/2000 | Balch | |
| 6,087,102 A | 7/2000 | Chenchik et al. | |
| 6,087,103 A | 7/2000 | Burmer | |
| 6,100,099 A | 8/2000 | Gordon et al. | |
| 6,103,479 A * | 8/2000 | Taylor ............................. 216/11 | |
| 6,107,059 A | 8/2000 | Hart | |
| 6,110,426 A | 8/2000 | Shalon et al. | |
| 6,121,048 A | 9/2000 | Zaffaroni et al. | |
| 6,122,408 A | 9/2000 | Fang et al. | |
| 6,124,102 A | 9/2000 | Fodor et al. | |
| 6,146,830 A | 11/2000 | Friend et al. | |
| 6,190,619 B1 | 2/2001 | Kilcoin et al. | |
| 6,190,908 B1 | 2/2001 | Kang | |
| 6,194,612 B1 | 2/2001 | Boger et al. | |
| 6,197,506 B1 | 3/2001 | Fodor et al. | |
| 6,197,599 B1 | 3/2001 | Chin et al. | |
| 6,225,047 B1 | 5/2001 | Hutchens et al. ................... 435/5 | |
| 6,303,344 B1 | 10/2001 | Patten et al. | |
| 6,316,186 B1 | 11/2001 | Ekins | |
| 6,329,209 B1 * | 12/2001 | Wagner et al. ................ 436/518 |
| 6,346,413 B1 | 2/2002 | Fodor et al. | |
| 6,350,369 B1 | 2/2002 | Lewis et al. | |
| 6,365,418 B1 | 4/2002 | Wagner et al. | |
| 6,391,625 B1 | 5/2002 | Park et al. | |
| 6,399,365 B2 | 6/2002 | Besemer et al. | |
| 6,403,320 B1 | 6/2002 | Read et al. | |
| 6,406,921 B1 | 6/2002 | Wagner et al. | |
| 6,416,952 B1 | 7/2002 | Pirrung et al. ..................... 435/6 | |
| 6,454,924 B2 | 9/2002 | Jedrzejewski et al. | |
| 6,475,808 B1 | 11/2002 | Wagner et al. | |
| 6,475,809 B1 | 11/2002 | Wagner et al. | |
| 6,531,283 B1 | 3/2003 | Kingsmore et al. | |
| 6,544,739 B1 | 4/2003 | Fodor et al. | |
| 6,576,478 B1 | 6/2003 | Wagner et al. | |
| 6,582,969 B1 | 6/2003 | Wagner et al. | |
| 6,596,545 B1 | 7/2003 | Wagner et al. | |
| 6,600,031 B1 | 7/2003 | Fodor et al. | |
| 6,610,482 B1 | 8/2003 | Fodor et al. | |
| 6,630,358 B1 | 10/2003 | Wagner et al. | |
| 6,635,311 B1 | 10/2003 | Mirkin et al. | |
| 6,682,942 B1 | 1/2004 | Wagner et al. | |
| 6,692,751 B1 | 2/2004 | Zebedee et al. | |
| 6,699,665 B1 | 3/2004 | Kim et al. | |
| 6,720,149 B1 | 4/2004 | Rava et al. | |
| 6,720,157 B2 | 4/2004 | Indermuhle et al. | |
| 6,780,582 B1 | 8/2004 | Wagner et al. | |
| 6,818,411 B2 | 11/2004 | Hutchens et al. | |
| 6,844,165 B2 | 1/2005 | Hutchens et al. | |
| 6,881,586 B2 | 4/2005 | Hutchens et al. | |
| 6,897,073 B2 | 5/2005 | Wagner et al. | |
| 6,899,137 B2 | 5/2005 | Unger | |
| 6,919,211 B1 | 7/2005 | Fodor et al. | |
| 6,943,034 B1 | 9/2005 | Winkler et al. | |
| 6,960,457 B1 | 11/2005 | Spudich et al. | |
| 7,132,251 B1 | 11/2006 | Markman et al. | |
| 2002/0106702 A1 | 8/2002 | Wagner | |
| 2002/0110932 A1 | 8/2002 | Wagner et al. | |
| 2002/0110933 A1 | 8/2002 | Wagner et al. | |
| 2002/0115225 A1 | 8/2002 | Wagner et al. | |
| 2002/0119579 A1 | 8/2002 | Wagner et al. | |
| 2002/0132272 A1 | 9/2002 | Wagner et al. | |
| 2002/0137053 A1 | 9/2002 | Ault-Riche et al. | |
| 2002/0164656 A1 | 11/2002 | Hoeffler et al. | |
| 2003/0003599 A1 | 1/2003 | Wagner et al. | |
| 2003/0017149 A1 | 1/2003 | Hoeffler et al. | |
| 2003/0073811 A1 | 4/2003 | Kozlowski et al. | |
| 2003/0138973 A1 | 7/2003 | Wagner et al. | |
| 2004/0048305 A1 * | 3/2004 | Kapeller-Libermann ........ 435/6 |
| 2004/0197931 A1 | 10/2004 | Indermuhle | |
| 2004/0241751 A1 | 12/2004 | Wagner et al. | |
| 2004/0248323 A1 | 12/2004 | Zhou et al. | |
| 2005/0008674 A1 | 1/2005 | Wagner et al. | |
| 2005/0014292 A1 | 1/2005 | Wagner et al. | |
| 2005/0026215 A1 | 2/2005 | Predki et al. | |
| 2005/0095646 A1 | 5/2005 | Sherman | |
| 2005/0100947 A1 | 5/2005 | Wagner et al. | |
| 2005/0118655 A1 | 6/2005 | Weinstock et al. | |
| 2005/0182242 A1 | 8/2005 | Snyder et al. | |
| 2005/0233473 A1 | 10/2005 | Cicero et al. | |
| 2005/0244854 A1 | 11/2005 | Cahill et al. | |
| 2006/0035387 A1 | 2/2006 | Wagner et al. | |
| 2006/0099704 A1 | 5/2006 | Predki et al. | |
| 2009/0324608 A1 * | 12/2009 | Meyers et al. ............. 424/158.1 |

FOREIGN PATENT DOCUMENTS

| | | |
|---|---|---|
| EP | 0 895 082 | 2/1999 |
| EP | 0972564 | 1/2000 |
| EP | 1086742 | 3/2001 |
| EP | 1 186 659 | 3/2002 |
| JP | 02272081 | 11/1990 |
| WO | WO 89/04675 | 6/1989 |
| WO | WO 89/10977 | 11/1989 |
| WO | WO 90/05144 | 5/1990 |
| WO | WO 92/01047 | 1/1992 |
| WO | WO 92/10588 | 6/1992 |
| WO | WO 92/20791 | 11/1992 |
| WO | WO 93/12248 | 6/1993 |

| | | |
|---|---|---|
| WO | WO 93/19172 | 9/1993 |
| WO | WO 95/35505 | 12/1995 |
| WO | WO 96/36436 | 11/1996 |
| WO | WO 97/32017 | 9/1997 |
| WO | WO 9742507 | 11/1997 |
| WO | WO 98/23948 | 6/1998 |
| WO | WO 98/27229 | 6/1998 |
| WO | WO 98/31830 A1 | 7/1998 |
| WO | WO 98/39481 | 9/1998 |
| WO | WO 98/43086 | 10/1998 |
| WO | WO 98/50773 | 11/1998 |
| WO | WO 98/53103 | 11/1998 |
| WO | WO 98/59360 | 12/1998 |
| WO | WO 98/59361 | 12/1998 |
| WO | WO 98/59362 | 12/1998 |
| WO | WO 99/11777 | 3/1999 |
| WO | WO 99/20749 | 4/1999 |
| WO | WO 99/28502 | 6/1999 |
| WO | WO 99/39210 | 8/1999 |
| WO | WO 9939210 | 8/1999 |
| WO | WO 9940434 | 8/1999 |
| WO | WO 99/45130 | 9/1999 |
| WO | WO 99/45149 | 9/1999 |
| WO | WO 99/57311 | 11/1999 |
| WO | WO 99/57312 | 11/1999 |
| WO | WO 00/06770 | 2/2000 |
| WO | WO 00/07024 | 2/2000 |
| WO | WO 00/20475 | 4/2000 |
| WO | WO 00/54046 | 7/2000 |
| WO | WO 00/63701 | 10/2000 |
| WO | WO 01/04265 | 1/2001 |
| WO | WO 01/14425 | 3/2001 |
| WO | WO 01/18545 | 3/2001 |
| WO | WO 01/29220 | 4/2001 |
| WO | WO 01/36681 | 5/2001 |
| WO | WO 01/57198 | 8/2001 |
| WO | WO 01/81924 | 11/2001 |
| WO | WO 01/83827 | 11/2001 |
| WO | WO 02/27327 | 4/2002 |
| WO | WO 02/36342 | 5/2002 |
| WO | WO 02/48676 | 6/2002 |
| WO | WO 02/053775 | 7/2002 |
| WO | WO 02/086491 | 10/2002 |
| WO | WO 02/092118 | 11/2002 |
| WO | WO 02/099099 | 12/2002 |
| WO | WO 03/018854 | 3/2003 |

OTHER PUBLICATIONS

Plowman et al., "The protein kinases of *Caenorhabditis elegans*: A model for signal transduction in multicellular organisms", Nov. 23, 1999, PNAS, 96 (24), pp. 13603-13610.*

Vanhaesebroeck et al., "Signaling by Distinct Classes of Phosphoinositide 3-Kinases", Nov. 25, 1999, Experimental Cell Research, vol. 253, Issue 1, pp. 239-254.*

Ashmarina et al., "Yeast glyceraldehyde-3-phosphate dehydrogenase. Evidence that subunit cooperativity in catalysis can be controlled by the formation of a complex with phosphoglycerate kinase", May 15, 1985, Eur. J. Biochem., 149(1), pp. 67-72.*

Abstract XP002291800, Derwent Publication Ltd., London, GB; AN 1997-011913.

Ahluwalia, et al, Biosens. Bioelectron. 7(3):207-214, 1992.

Ames et al., "Conversion of murine Fabs isolated from a combinatorial phage display library to full length immunoglobulins", 1995, J. Immunol. Methods 184:177-86.

Baecher-Allan et al., "Differential epitope expression of Ly-48 (mouse leukosialin)." Immunogenetics. 1993;37(3): 183-92.

Bailis, J. M., & Roeder, G. S. Synaptonemal complex morphogenesis and sisterchromatid cohesion require Mek1-dependent phosphorylation of a meiotic chromosomal protein. Genes & Dev. 12, 3551-3563 (1998).

Barral et al. "Niml-related kinases coordinate cell cycle progression with the organization of the peripheral cytoskeleton in yeast." Genes & Dev. 13, 176-187 (1999).

Bhatia, et al, Anal. Biochem. 178(2):408-413, 1989.

Blachere et al., "Heat shock protein vaccines against cancer" 1993, J. Immunotherapy 14:352-6.

Bussow et al., "A human cDNA library for high-throughput protein expression screening." 2000, Genomics 65:1.

Caveman, ""I'll have a genome with chips, please". By Caveman." 2000, J. Cell Sci. 113:3543.

Cha et al. Expression of fused protein, human interleukin-2 simplified as a fusion with green fluorescent protein, in suspended Sf-9 insect cells" J. Biotechnology 69, 9-17. (1999). Early work presented at " Annual Meeting of The American Institute of Chemical Engineers, Los Angeles, CA, Nov. 1997.

Christendat et al. "Structural proteomics: prospects for high throughput sample preparation." Prog Biophys Mol Biol. 2000;73(5):339-45. Review. No abstract available.

Christendat et al., "Structural proteomics of an archaeon." Nat Struct Biol. Oct. 2000;7(10):903-9.

Cohen P. "Classification of protein-serine/threonine phosphatases: identification and quantitation in cell extracts." Methods Enzymol. 1991;201:389-98. Review. No abstract available.

Cohen, et al., "An artificial cell-cycle inhibitor isolated from a combinatorial library.", Proc. Natl. Acad. Sci. USA, 95:14272-7, 1998.

Collioud et al. (1993). Oriented and covalent immobilization of target molecules to solid supports: Synthesis and application of a light-activatable and thiol-reactive cross-linking reagent. Bioconjugate Chem. 4:528-536.

Couchman et al., "p53lyn and p56lyn: a new signaling pathway in human endometrium and endometrial adenocarcinomas.", J Soc Gynecol Investig. Mar.-Apr. 1997;4(2):103-9.

Cupo JF. "Electrophoretic analysis of nuclear matrix proteins and the potential clinical applications.", J Chromatogr. Sep. 13, 1991;569(1-2):389-406.

Davies and Benzer: Generation of cDNA expression libraries enriched for in-frame sequences PNAS v. 94, 2128-2132, 1997.

Davies et al. "Profiling of amyloid beta peptide variants using SELDI Protein Chip arrays." Biotechniques. Dec. 1999;27(6):1258-61.

Dawson et al., "Peptide-derived self-assembled monolayers: adsorption of N-stearoyl I-Cysteine methyl ester on gold," Journal of Molecular Recognition, 10:18-25 (1997).

DeRisi et al., Exploring the metabolic and genetic control of gene expression on a genomic scale. Science 278, 680-686 (1997).

Duschl et al., "Surface engineering: optimization of antigen presentation in self-assembled monolayers," Biophysical Journal, 70:1985-1995 (1996).

Dzgoev et al "Microformat imaging Elisa for pesticide determination" Anal. Chem. 68(19):3364 (1996).

Ekins "Ligand assays" from electrophoresis to miniaturized microarrays Clin. Chem. 44(9):2015-2030 (1998).

Ekins et al., "Multianalyte microspot immunoassay—microanalytical "compact disk" of the future", Clin Chem. Nov. 1991;37(11):1955-67.

Ekins et al., Multianalyte microspot immunoassay. The microanalytical 'compact disk' of the future. Ann Biol Clin (Paris). 1992;50(5):337-53.

Ekins, et al., Clinica Chimica Acta., 194:91-114, 1990.

Ferrigno et al. "Regulated nucleo/cytoplasmic exchange of HOGI MAPK requires the importin beta homologs NMD5 and XPO1." EMBO J. 17, 5606-5614 (1998).

Fields et al., "Functional genomics." Proc. Natl. Acad. Sci. 96, 8825-26 (1999).

Fini et al., 1999, "Development of a chemiluminescence competitive PCR for the detection and quantification of parvovirus B19 DNA using a microplate luminometer", Clin Chem. 45(9):1391-6.

Fitch, W. M. & Margoliash, E. Construction of phylogenetic trees. Science. 155, 279-284 (1967).

Freij-Larsson, et al, Biomaterials 17(22):2199-2207, 1996.

Fukuda, et al., Nucleic Acids Symp. Ser., (37):237-8, 1997.

Ganz et al., "Characterization of plasminogen binding to human capillary and arterial endothelial cells.", Biochem Cell Biol. Jul. 1991;69(7):442-8.

Geohegan et al. "Fluorescence-based continuous assay for the aspartyl protease of human immunodeficiency virus-1" FEBS 262:119-122 (1990).

Goffeau, A., et al. Life with 6000 genes. Science 274, 563-567 (1996).

Gonnet, G. H., Cohen, M. A., and Benner, S. A. Exhaustive matching of the entire protein sequence database. Science. 256, 1443-1445 (1992).

Guenthner and Hart, 1998, "Quantitative, competitive PCR assay for HIV-1 using a microplate-based detection system", Biotechniques 24(5):810-6.

Guerra et al., 2000, Biosci. Rep. 20: 41.

Hegner et al., "Ultralarge atomically flat template-stripped Au surfaces for scanning probe microscopy," Surface Science, 291:39-46 (1993).

Heyman, J. A., et al. Genome-scale cloning and expression of individual open reading frames using topoisomerase 1-mediated ligation. Genome Res. 9, 383-392 (1999).

Higgins, D. G., Thompson, J. D., and Gibson, T. J. Using CLUSTAL for multiple sequence alignments. Methods Enzymol. 266, 383-402 (1996).

Ho, U., Mason, S., Kobayashi, R., Heokstra, M., and Andrew, B. Role of the casein kinase 1 isoform, Hrr25, and the cell cycle-regulatory transcription factor, SBR, in the transcriptional response to DNA damage in *Saccharomyces cerevisiae*. Proc. Natl. Acad. Sci. 94, 581-586 (1997).

Holly et al. PAK-family kinases regulate cell and actin polarization throughout the cell cycle of *Saccharomyces cerevisiae*. J. Cell Biol. 147, 845-856 (1999).

Horak et al. "ChIP-chip: a genomic approach for identifying transcription factor binding sites." Methods Enzymol. 2002;350:469-83. No abstract available.

Huang RP. "Detection of multiple proteins in an antibody-based protein microarray system." J Immunol Methods. Sep. 1, 2001;255(1-2):1-13.

Hudson, J. R., et al. The complete set of predicted genes from *Saccharomyces cerevisiae* in a readily usable form. Genome Res. 7, 1169-1173 (1997).

Hunter, T. & Sefton, B. M. Protein phosphorylation. Meth. in Enzym. 200, 35-83 (1991).

Ito et al., "Toward a protein-protein interaction map of the budding yeast: A comprehensive system to examine two-hybrid interactions in all possible combinations between the yeast proteins." Proc. Natl. Acad. Sci. USA. 97, 1143 (2000).

Jaquenoud, M., Gulli, M. P., Peter, K., and Peter, M. The Cdc42p effector Gic2p is targeted for ubiquitin-dependent degradation by the SCFGrr1 complex. EMBO J. 17, 5360-5373 (1998).

Jona G, Snyder M., Recent developments in analytical and functional protein microARRAYs. Curr Opin Mol Ther. Jun. 2003;5(3):271-7. Review.

Jones et al. "Microminiaturized immunoassays using atomic force microscopy and compositionally patterned antigen arrays" Anal. Chem. 70(7):1223-1241 (1998).

Jonsson et al. "Immobilization of immunoglobulins on silica surfaces. Kinetics of immobilization and influence of ionic strength." Biochem J. Apr. 15, 1985;227(2):373-8.

Kaouass, M., et al. The STK2 gene, which encodes a putative Ser/Thr protein kinase, is required for high-affinity spermidine transport in *Saccharomyces cerevisiae*. Mol. Cell Biol. 17, 2994-3004 (1997).

Kaplan et al. "Selection of multiple human immunodeficiency virus type I variants that encode viral proteases with decresed sensitivity to an inhibitor of the viral inhibitor" Proc. Natl. Acad. Sci. USA 91:5597-5601 (1994).

Kemeny "Enyme-linked immunoassays" In Immuno Chemistry I (eds Johnstone and Turner) p. 147-175 (Nov. 1997).

Kettleborough et al., "Isolation of tumor cell-specific single-chain Fv from immunized mice using phage-antibody libraries and the reconstruction of whole antibodies from these antibody fragments." Eur. J. Immunol. 24:952-8 (1994).

Knezevic et al., 2001, Proteomics 1, 1271-8.

Kodadek T. "Protein microarrays: prospects and problems." Chem Biol. Feb. 2001;8(2):105-15.

Kricka "Miniaturization of analytical systems" Clin. Chem. 44(9):2008-2014 (1998).

Kumar et al. "An integrated approach for finding overlooked genes in yeast." Nat Biotechnol. Jan. 2002;20(1):58-63.

Lakey et al., "Measuring protein-protein interactions", Curr Opin Struct Biol. 8:119-23 (1998).

Lijnen et al. Screening panels of monoclonal antibodies using phage-displayed antigen. Anal Biochem. Jun. 1, 1997;248(2):211-5.

Lipman, D. J. & Pearson, W. R. Rapid and sensitive protein similarity searches. Science. 277, 1435-1441 (1985).

Loeb et al. "Complete mutegenesis of the HIV-1 protease" Nature 340:397-400 (1989).

Louis et al. "Autoprocessing of the HIV-1 protease using purified wild-type and mutated fusion proteins expressed at high levels in *Eschericia coli*" Eur. J. Biochem. 199:361-369 (1991).

Luscombe et al. "ExpressYourself: A modular platform for processing and visualizing microARRAY data." Nucleic Acids Res. Jul. 1, 2003;31(13):3477-82.

MacBeath et al. "Printing proteins as microarrays for high-throughput function determination." Science 289, 1760 (2000).

Madden, K., Sheu, Y.-J., Baetz, K., Andrews, B., and Snyder, M. SBF cell cycle regulator as a target of the yeast PKC-MAP kinase pathway. Science 275, 1781-1784 (1997).

Madoz-Gurpide et al. "Protein based microarrays: a tool for probing the proteome of cancer cells and tissues." Proteomics. Oct. 2001;1(10):1279-87.

Maier et al.., "Automated array technologies for gene expression profiling", Drug Discovery Today, 2(8), 315-324, (1997).

Malathi, K., Xiao, Y., and Mitchell, A. P. Catalytic roles of yeast GSK3beta/shaggy homolog Rim11p in meiotic activation. Genetics 153, 1145-1152 (1999).

Marks et al. "By-passing immunication-Human antibodies from V-gene libraries displayed on phage" J. Mol. Biol. 222:581-597 (1991).

Marshall et al., "DNA chips: an array of possibilities." Nat Biotechnol. Jan. 1998;16(1):27-31.

Mathys, et al., Gene 231:1-13, 1999; Evans, et al., Protein Science 7:2256-2264, 1998).

Memeny. Enzyme-linked immunoassays. In Immuno-Chemistry 1 (eds Johnstone and Turner). p. 147-175, Nov. 1997.

Menees, T. M., Ross-MacDonald, P. B., and Roeder, G. S. MEI4, a meiosis-specific yeast gene required for chromosome synapsis. Mol. Cell Biol. 12, 1340-1351 (1992).

Michaud et al., "Proteomic approaches for the global analysis of proteins. Biotechniques." Dec. 2002;33(6):1308-16. Review.

Moore et al. "Peptide substrates and indibitors of HIV-1 protease" Biochem. Biophys. Res. Com. 159:420-425 (1989).

Mylin et al. Regulated GAL4 expression cassette providing controllable and high-level output from high-copy galactose promoters in yeast. Methods Enzymol. 185, 297-308 (1990).

Nock, "Reversible, site-specific immobilization of polyarginine-tagged fusio proteins on mice surfaces," FEBS, 414-233-238 (1997).

Owen, D. J., Noble, M. E., Garman, E. F., Papageorgiou, A. C., and Johnson, L. N. Two structures of the catalytic domain of phosphorylase kinase: an active protein kinase complexed with substrate analogue and product. Structure, 3, 467-474 (1995).

Pale-Grosdemange et al. "Formation of self-assembled monolayers by chemisorption of derivatives of oligo(ethylene glycol) of structure HS(CH2)11(OCH2CH2)mOH on gold" J. Am. Chem. Soc. 113(1)12-20 (1991).

Palladino et al., 1987, Cancer Res. 47:5074-9.

Pearson, W. R. & Lipman, D. J. Improved tools for biological sequence comparison. Proc. Natl. Acad. Sci. 85, 2444-2448 (1988).

Persic et al., 1997, Gene 187:9-18.

Pham, et al. "Human Interleukin-2 Production in Insect (*Trichoplusia ni*) Larvae: Effects and Partial Control of Proteolysis", Biotechnology and Bioengineering vol. 62(2) pp. 175-182; Jan. 20, 1999.

Plowman et al. "The protein kinases of *Caenorhabditis elegans*: A model for signal transduction in multicellular organisms. " Proc. Natl. Acad. Sci. 96, 13603-12610 (1999).

Prime et al., "Self-assembled organic monolayers: model systems for studying absorption of proteins at surfaces," Science, 252:1164-1167 (1991).

Ragg et al., FASEB, (9)73-80, Jan. 1995.

Ramsay G., "DNA chips: state-of-the art.", Nat Biotechnol. Jan. 1998;16(1):40-4.

Richman, T. J., Sawyer, M. M., and Johnson, D. 1. The Cdc42p GTPase is involved in a G2/M morphogenetic checkpoint regulating the apical-isotropic switch and nuclear division in yeast. J. Biol. Chem. 274, 16861-16870 (1999).

Roberts and Szostak, Proc. Natl. Acad. Sci. USA, 94:12297-302, 1997.

Roberts et al. "Rationale design of peptide-based HIV proteinase inhibitors" Science 248:358-361 (1990).

Roemer, T. K., et al. Selection of axial growth sites in yeast requires Ax12p, a novel plasma membrane glycoprotein. Genes & Dev. 10, 777-793 (1996).

Rowe et al. "Array biosensor for simultaneous identification of bacterial, viral and protein analytes" Anal. Chem. 71(17):3846-3852 (1999).

Santos, T. & Hollingsworth, N. M. Redip, A MEK1-dependent phosphoprotein that physically interacts with Hop1p during meiosis in yeast. J. Biol. Chem. 274, 178310 1790 (1999).

Schuh et al., "Determination of monoclonal antibody specificity by immunoadsorption and western blotting.", J Immunol Methods. Jul. 31, 1992;152(1):59-67.

Sigal et al. (1996). A self-assembled monolayer for the binding and study of histidine-tagged proteins by surface plasmon resonance. Anal. Chem. 68:490-497.

Silzel et al. "Mass-sensing, multianalyte microarray immunoassay with imaging detection" Clin. Chem. 44(9):2036-2043 (1998).

Sobel et al., "A highly divergent gamma-tubulin gene is essential for cell growth and proper microtubule organization in *Saccharomyces cerevisiae.*" J. Cell Biol. 131, 1775-1788 (1995).

Stevenson et al., Biomarkers, (2)63-65, 1997.

Sundberg et al., "Spatially-addressable immobilization of macromolecules on solid supports," J. Am. Chem. Soc., 117:12050-12057 (1995).

Uetz et al., "A comprehensive analysis of protein-protein interactions in *Saccharomyces cerevisiae.*" Nature, Feb. 10; 403 (6770) 623-7 (2000).

Wagner et al., "Covalent immobilization of native biomolecules onto Au(111) via N-hydroxysuccinimide ester functionalized self-assembled monolayers for scanning probe microscopy," Biophysical Journal, 70:2052-2066 (1996).

Wagner et al., "Formation and in Situ modification of monolayers chemisorbed on ultraflat template-stripped gold surfaces," Langmuir, 11(10):3867-3875 (1995).

Wagner et al., Journal of Structural Biology, 1997, 119:189-201.

Weiner et al. "Site-directed mutagenesis of double-stranded DNA by the polymerase chain reaction" Gene 151:119-123 (1994.

Weinert, T. A. & Hartwell, L. H. Cell cycle arrest of cdc mutants and specificity of the RAD9 checkpoint. Genetics 134, 63-80 (1993).

Woo et al., Methods in Enzy,mology, vol. 68, 389-395, 1979.

Wu et al. "Structural basis for a specificity of retroviral proteases" Biochemistry 37:4518-4526 (1998).

Wurgler-Murphy et al., "Regulation of the *Saccharomyces cerevisiae* HOG1 mitogen-activated protein kinase by the PTP2 and PTP3 protein tyrosine phosphatases." Mol. Cell Biol. 17, 1289-1297 (1997).

Xia, Y. & Whitesides, G. M. Angew. Chem. Int. Ed. 37, 550-(1997).

Zhang et al., "Protein tyrosine phosphatases: mechanism of catalysis and substrate specificity." Adv Enzymol Relat Areas Mol Biol. 1994;68:1-36. Review.

Zhu et al. "Global analysis of protein activities using proteome chips." Science. Sep. 14, 2001;293(5537):2101-5. Epub Jul. 26, 2001.

Zhu et al. "Protein array and micro array s" Curr Opin Chem Biol. Feb. 2001;5(1):40-5. Review.

Zhu et al. "Protein chip technology." Curr Opin Chem Biol. Feb. 2003;7(1):55-63. Review.

Zhu et al. "Proteomics." Annu Rev Biochem. 2003;72:783-812. Review.

Ziegler et al., Cucumber mosaic cucumovirus antibodies from a synthetic phage display library. Virology. Dec. 1, 1995;214(1):235-8.

Aguas et al., "Cross-reactivity and sequence homology between the 65-kilodalton mycobacterial heat shock protein and human lactoferrin, transferrin, and DR beta subsets of major histocompatibility complex class II molecules." Infection & Immunity; vol. 58; 1461-1470 (1990).

Brott et al. "GTPase-activating protein interactions with the viral and cellular Src kinases.", PNAS, 88 (3): 755. (1991).

Bussow, "A method for global protein expression and antibody screening on high-density filters of an arrayed cDNA library.", Nucleic Acids Research 26:5007-5008 (1998).

Golding et al., "Identification of homologous regions in human immunodeficiency virus I gp41 and human MHC class II beta 1 domain. I. Monoclonal antibodies against the gp41-derived peptide and patients' sera react with native HLA class II antigens, suggesting a role for autoimmunity in the pathogenesis of acquired immune deficiency syndrome." J of Experimental Medicine; vol. 167; 914-923 (1988).

Haab, "Advances in protein microarray technology for protein expression and interaction profiling.", Current Opinion in Drug Discovery and Development 4:116-123 (2001).

Kanan et al., " Lectin Immunoassay for Macrophage-activating Factor (Gc-MAF) Produced by Deglycosylation of Gc-Globulin: Evidence for Noninducible Generation of Gc-MAF", Clinical Chem. 46(3) 412-430. 2000.

Piehler J et al., "Multianalyte determination with a direct optical miltiantibody detection system (Proceedings Paper) ", SPIE V. 2504; 185-94 (1995).

Venter, "The sequence of the human genome.", Science 29:1304-1351 (2001).

Wilbur et al. "Rapid similarity searches of nucleic acid and protein data banks." Proc Natl Acad Sci U S A. Feb. 1983;80(3):726-30.

Office Action dated Oct. 23, 2007, U.S. Appl. No. 10/477,329, filed Mar. 10, 2005, "Global analysis of protein activities using proteome chips".

Office Action dated Jul. 12, 2006, U.S. Appl. No. 10/477,329, filed Mar. 10, 2005, "Global analysis of protein activities using proteome chips".

Office Action dated Jan. 25, 2006, U.S. Appl. No. 10/477,329, filed Mar. 10, 2005, "Global analysis of protein activities using proteome chips".

Águas, A., et al., "Cross-Reactivity and Sequence Homology between the 65-Kilodalton Mycobacterial Heat Shock Protein and Human Lactoferrin, Transferrin, and $DR_\beta$ Subsets of Major Histocompatibility Complex Class II Molecules," *Infect. Immun.* 58:1461-1470, American Society for Microbiology (1990).

Brott, B.K., et al., "GTPase-activating protein interactions with the viral and cellular Src kinases," *Proc. Natl. Acad. Sci. U.S.A.* 88:755-759, National Academy of Sciences (1991).

Büssow, K., et al., "A method for global protein expression and antibody screening on high- density filters of an arrayed cDNA library," *Nucleic Acids Res.* 26:5007-5008, Oxford University Press (1998).

Coito, C., et al., "High-Throughput Screening of the Yeast Kinome: Identification of Human Serine/Threonine Protein Kinases That Phosphorylate the Hepatitis C Virus NS5A Protein," *J. Virol.* 78:3502-3513, American Society for Microbiology (Apr. 2004).

Eickhoff, H., et al., "Protein Array Technology: The Tool to Bridge Genomics and Proteomics," *Adv. Biochem. Eng. Biotechnol.* 77:103-112, Springer Verlag (Jan. 2002).

Ge, H., "UPA, a universal protein array system for quantitative detection of proteinprotein, protein—DNA, protein—RNA and protein—ligand interactions," *Nucleic Acids Res.* 28:e3, Oxford University Press (Jan. 2000).

Golding, H., et al., "Identification of Homologous Regions in Human Immunodeficiency Virus I gp41 and Human MHC Class II β 1 Domain. I. Monoclonal Antibodies Against the gp41-derived Peptide and Patients' Sera React With Native HLA Class II Antigens, Suggesting a Role for Autoimmunity in the Pathogenesis of Acquired Immune Deficiency Syndrome," *J. Exp. Med.* 167:914-923, Rockefeller University Press (1988).

Groll, J., et al., "Biofunctionalized, Ultrathin Coatings of Cross-Linked Star-Shaped Poly(ethylene oxide) Allow Reversible Folding of Immobilized Proteins," *J. Am. Chem. Soc. 126*:4234-4239, American Chemical Society (Apr. 2004).

Hunter, T., and Plowman, G.D., "The protein kinases of budding yeast: six score and more," *Trends Biochem. Sci.* (*TIBS*) 22:18-22, Elsevier Trends Journals (1997).

Lee, M.G., and Nurse, P., "Complementation used to clone a human homologue of the fission yeast cell cycle control gene cdc2," *Nature* 327:31-35, Nature Publishing Company (1987).

Lueking, A., et al., "Protein Microarrays for Gene Expression and Antibody Screening," *Anal. Biochem.* 270:103-111, Academic Press (May 1999).

Manning, G., et al., "Evolution of protein kinase signaling from yeast to man," *Trends Biochem. Sci.* 27:514-520, Elsevier Trends Journals (Oct. 2002).

Manning, G., et al., "The Protein Kinase Complement of the Human Genome," *Science* 298:1912-1934, American Association for the Advancement of Science (Dec. 2002).

Piehler, J., et al., "Multianalyte determination with a direct optical miltiantibody detection system," *Pro.c Soc. Photo. Opt. Instrum. Eng.* 2504:185-194, SPIE (1995).

Servagent-Noinville, S., et al., "Conformational Changes of Bovine Serum Albumin Induced by Adsorption on Different Clay Surfaces: FTIR Analysis," *J. Colloid Interface Sci.* 221:273-283, Academic Press (Jan. 2000).

Tleugabulova, D., et al., "Evidence for the denaturation of recombinant hepatitis B surface antigen on aluminium hydroxide gel," *J. Chromatogr. B Biomed. Sci. Appl.* 720:153-163, Elsevier (1998).

Wilbur, W.J., et al., "Rapid similarity searches of nucleic acid and protein data banks," *Proc. Natl. Acad. Sci. U.S.A.* 80:726-730, National Academy of Sciences (1983).

Anderson, K.S. and Labaer, J., "The Sentinel Within: Exploiting the Immune System for Cancer Biomarkers," *J. Proteome Res.* 4(4):1123-33, American Chemical Society, United States (Jul.-Aug. 2005).

Bold, R.J. and Donoghue, D.J., "Biologically Active Mutants with Deletions in the v-*mos* Oncogene Assayed with Retroviral Vectors," *Mol. Cell. Biol.* 5(11):3131-8, American Society for Microbiology, United States (Nov. 1985).

Hanks, S.K., et al., "The Protein .Kinase Family: Conserved Features and Deduced Phylogeny of the Catalytic Domains," *Science* 241(4861):42-52, American Association for the Advancement of Science, United States (Jul. 1, 1988).

Hanks, S.K., "Genomic analysis of the eukaryotic protein kinase superfamily: a perspective," *Genome Biol.* 4(5):111, BioMed Central Ltd., England (2003; Epub Apr. 29, 2003).

Hubbard, S.R., et al., "Crystal structure of the tyrosine kinase domain of the human insulin receptor," *Nature* 372(6508):746-54, Nature Publishing Group, England (Dec. 22, 1994).

Morrison, D.K., et al., "Protein Kinases and Phosphatases in the Drosophila Genome," *J. Cell. Biol.* 150(2):F57-F62, Rockefeller University Press, United States (Jul. 24, 2000).

Sadowski, I. and Pawson, T., "Catalytic and non-catalytic domains of the *Fujinami sarcoma* virus P130$^{gag\text{-}fps}$ protein-tyrosine kinase distinguished by the expression of v-*fps* polypeptides in *Escherichia coli*," *Oncogene* 1:181-91, The Macmillan Press Ltd, England (1987).

Shaw, G., "Cheaper Chips Find a Good Fit with Hit Validation," *Drug Discovery & Development*, www.dddmag.com, accessed at http://www.dddmag.com/cheaper-chips-find-a-good-fit.aspx, published Feb. 3, 2005, accessed on May 6, 2011, 3 pages.

Yaciuk, P. and Shalloway, D., "Features of the pp60$^{v\text{-}src}$ Carboxyl Terminus That Are Required for Transformation," *Mol. Cell. Biol.* 6(8):2807-19, American Society for Microbiology, United States (Aug. 1986).

Zhu, H., et al., "Analysis of yeast protein kinases using protein chips," *Nat. Genet.* 26(3):283-9, Nature America Inc., United States (Nov. 2000).

Office Action mailed Jun. 6, 2008, in U.S. Appl. No. 10/477,329, Snyder et al., with a 35 U.S.C. § 371(c) date of Mar. 10, 2005.

Office Action mailed Mar. 5, 2009, in U.S. Appl. No. 10/477,329, Snyder et al., with a 35 U.S.C. § 371(c) date of Mar. 10, 2005.

Office Action mailed Nov. 18, 2009, in U.S. Appl. No. 10/477,329, Snyder et al., with a 35 U.S.C. § 371(c) date of Mar. 10, 2005.

Office Action mailed Oct. 1, 2010, in U.S. Appl. No. 10/477,329, Snyder et al., with a 35 U.S.C. § 371(c) date of Mar. 10, 2005.

Office Action mailed Dec. 2, 2010 in Canadian Patent Application No. 2,408,291, filed May 4, 2001.

Notice of Reasons for Rejection mailed Feb. 1, 2011 in Japanese Patent Application No. 2001-580434, filed May 4, 2001.

Martzen, et al. (Nov. 5, 1999). A Biochemical Genomics Approached for Identifying Genes by the Activity of Their Products. *Science*, vol. 286, pp. 1153-1155. Retrieved on Mar. 28, 2011 from www.sciencemag.org.

Arenkov et al., 2000, "Protein microchips: use for immunoassay and enzymatic reactions", Anal Biochem. 278(2):123-131.

Bieri et al., 1999, Micropatterned immobilization of a G protein-coupled receptor and direct detection of G protein activation. Nat Biotechnol. Nov. 1999;17(11):1105-1108.

Cohen et al., 1999, "A microchip-based enzyme assay for protein kinase A", Anal Biochem. 273(1):89-97.

Emili et al., 2000, "Large-scale functional analysis using peptide or protein arrays", Nat Biotechnol. 18(4):393-397.

Hatch et al., 1999, "Rolling circle amplification of DNA immobilized on solid surfaces and its application to multiplex mutation detection", Genet Anal. 15(2):35-40.

Jackman et al., 1999, "Using elastomeric membranes as dry resists and for dry lift-off", Langmuir. 15:2973-2984.

Kane et al., 1999, "Patterning proteins and cells using soft lithography", Biomaterials. 20(23-24):2363-2376.

Lueking et al., 1999, "Proein Microarrays for Gene Expression and Antibody Screening", Analytical Biochem 270: 103-111.

Martzen et al., 1999, "A biochemical genomics approach for identifying genes by the activity of their products", Science 286(5442):1153-1155.

Mitchell et al., 1993, "Vectors for the inducible overexpression of glutathione S-transferase fusion proteins in yeast", Yeast. 9(7):715-722.

Pandy et al., 2000, "Proteomics to study genes and genomes", Nature 405:837-846.

Peraldi et al., 1994, "Protein-tyrosine-phosphatase 2C is phosphorylated and inhibited by 44-kDa nitrogen-activated protein kinase" Light-generated oligonucleotide arrays for rapid DNA sequence analysis. Proc Natl Acad Sci U S A. May 24, 1994;91(11):5002-5006.

Rogers et al., 1999, "Immobilization of oligonucleotides onto a glass support via disulfide bonds: A method for preparation of DNA microarrays", Anal Biochem. 266(1):23-30.

Stimpson et al., 1995, Real-time detection of DNA hybridization and melting on oligonucleotide arrays by using optical wave guides Proc Natl Acad Sci U S A. 92(14):6379-83.

Xia et al., 1996, "Complex Optical Surfaces Formed by Replica Molding Against Elastomeric Masters", Science. 273(5273):347-349.

Zhu et al., 2000, "Analysis of yeast protein kinases using protein chips", Nat Genet. 26(3):283-289.

\* cited by examiner

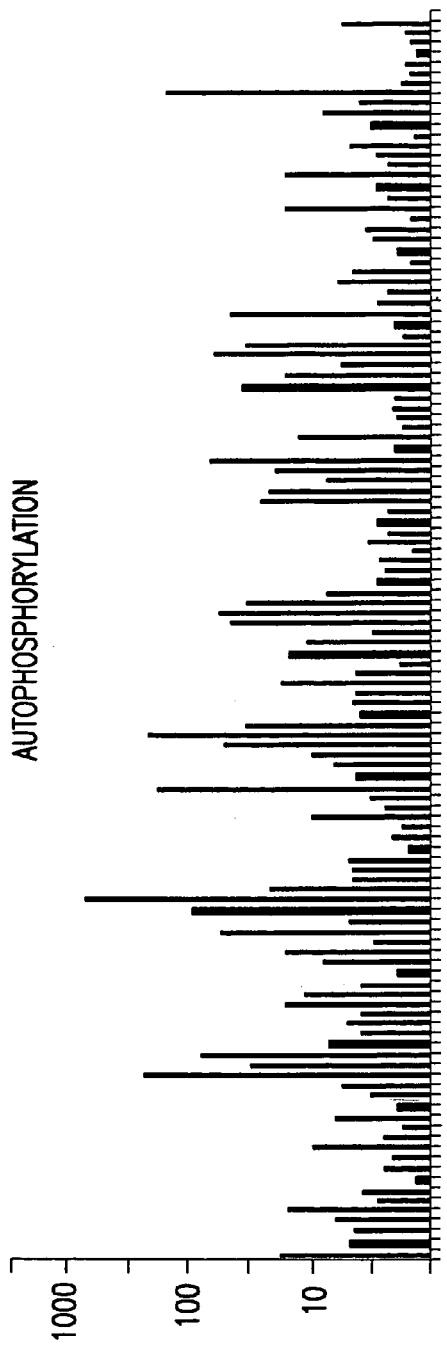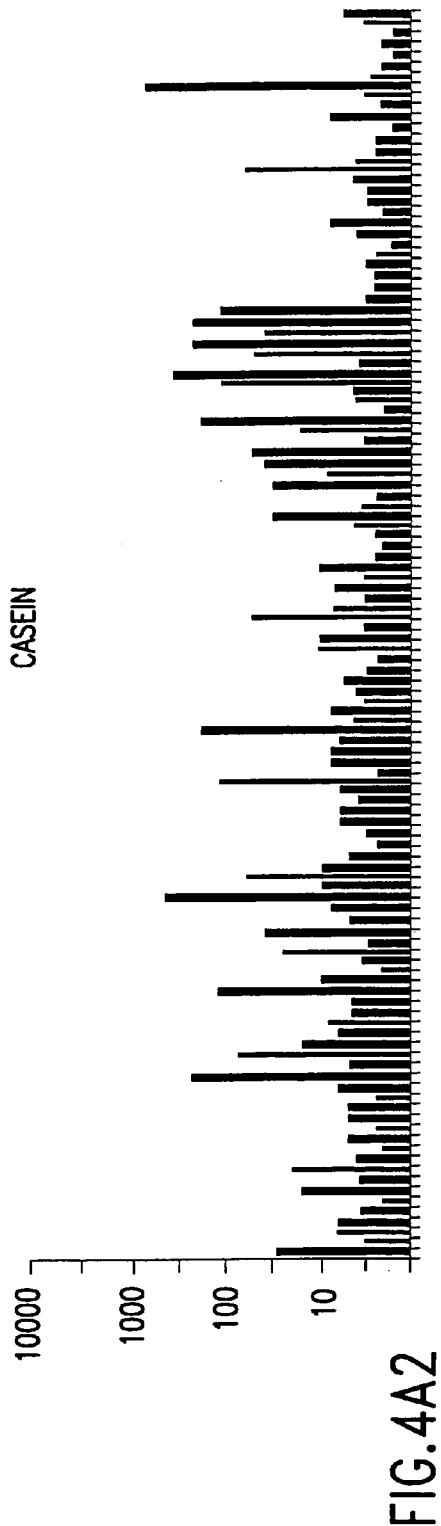

Figure 3:
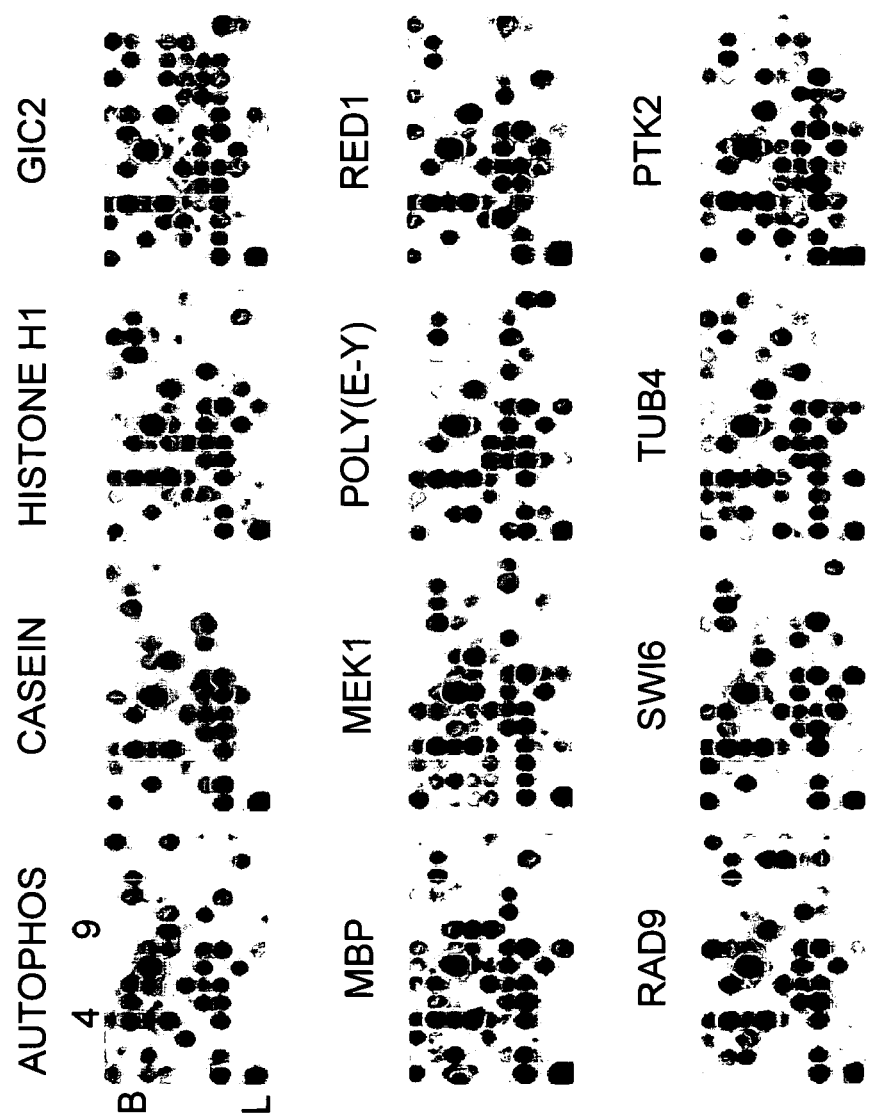

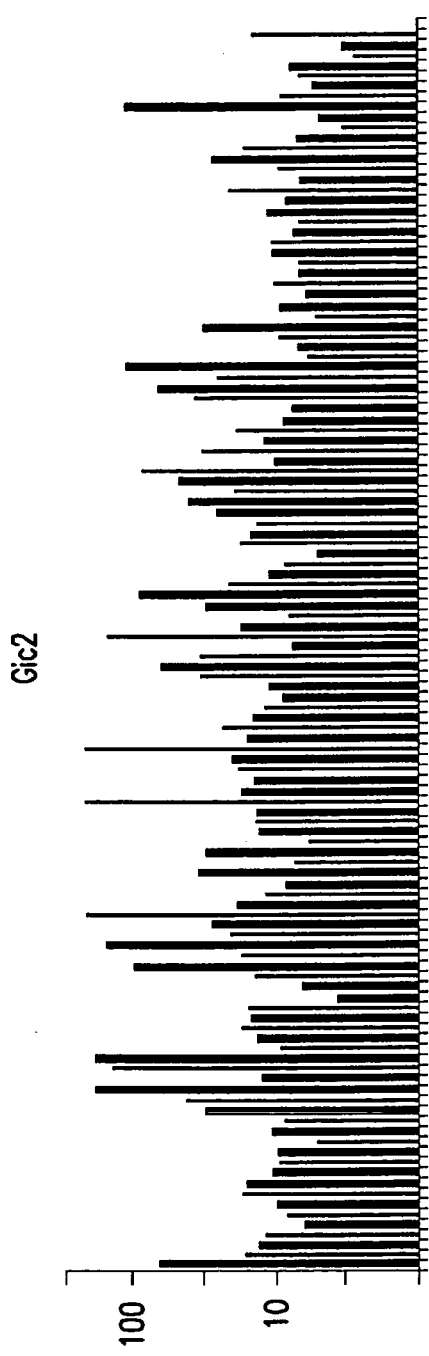
FIG. 4A3
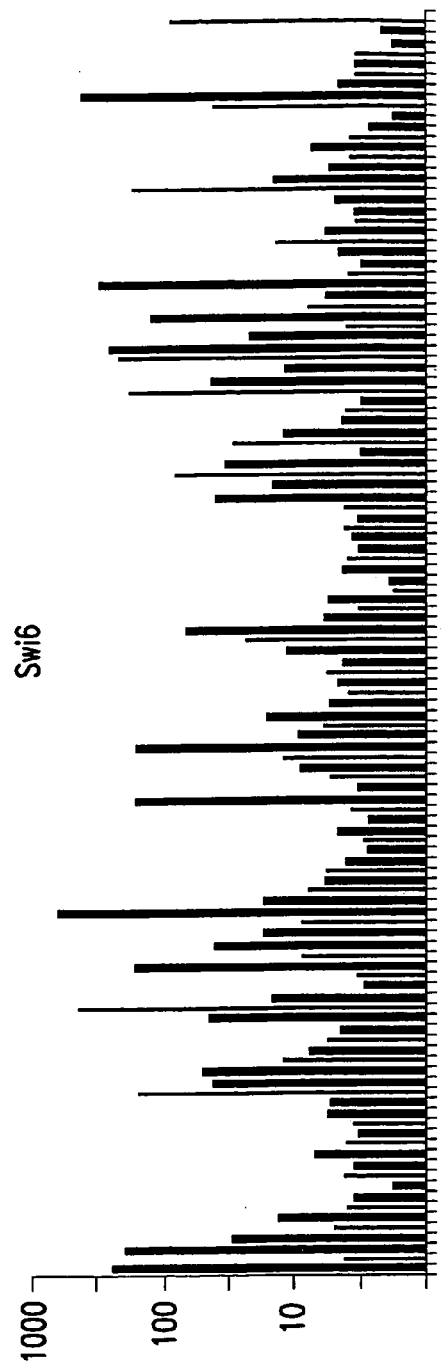
FIG. 4A4

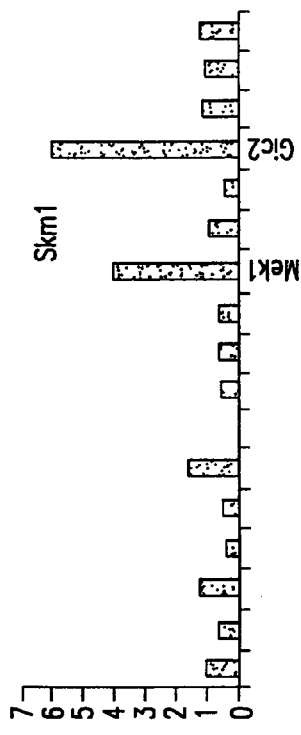
FIG.4B2
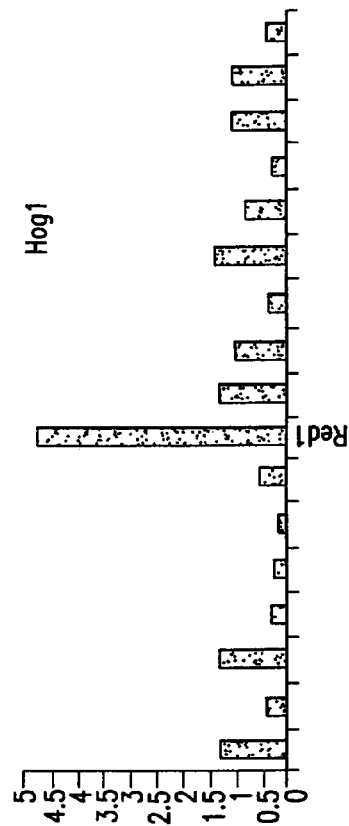
FIG.4B4
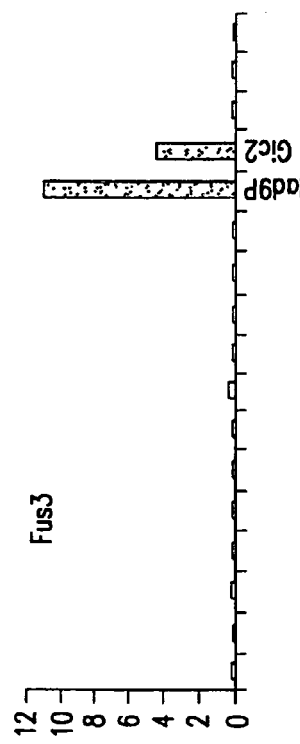
FIG.4B1
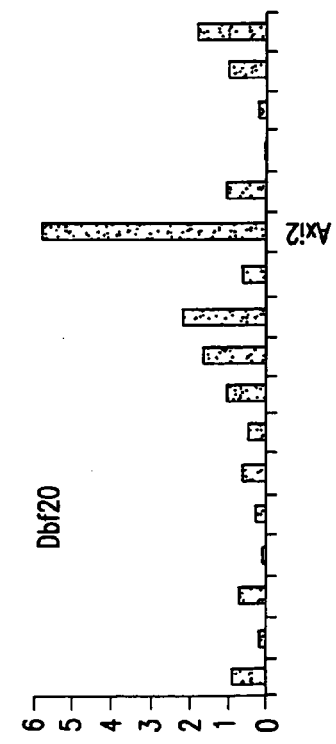
FIG.4B3

PROTEIN CHIPS FOR HIGH THROUGHPUT SCREENING OF PROTEIN ACTIVITY

This application claims the benefit under 35 U.S.C. §119 (e) of U.S. provisional patent application Ser. No. 60/201,921, filed on May 4, 2000, and U.S. provisional patent application Ser. No. 60/221,034, filed on Jul. 27, 2000, each of which is incorporated herein, by reference, in its entirety.

This invention was made with government support under grant numbers DARPA/ONR R13164-41600099 and NIH (National Institutes of Health) RO1CA77808. The government has certain rights in the invention.

I. FIELD OF THE INVENTION

The present invention relates to protein chips useful for the large-scale study of protein function where the chip contains densely packed reaction wells. The invention relates to methods of using protein chips to assay simultaneously the presence, amount, and/or function of proteins present in a protein sample or on one protein chip, or to assay the presence, relative specificity, and binding affinity of each probe in a mixture of probes for each of the proteins on the chip. The invention also relates to methods of using the protein chips for high density and small volume chemical reactions. Also, the invention relates to polymers useful as protein chip substrates and methods of making protein chips. The invention further relates to compounds useful for the derivatization of protein chip substrates.

II. BACKGROUND OF THE INVENTION

The sequencing of entire genomes has resulted in the identification of large numbers of open reading frames (ORFs). Currently, significant effort is devoted to understanding gene function by mRNA expression patterns and by gene disruption phenotypes. Important advances in this effort have been possible, in part, by the ability to analyze thousands of gene sequences in a single experiment using gene chip technology. However, much information about gene function comes from the analysis of the biochemical activities of the encoded protein.

Currently, these types of analyses are performed by individual investigators studying a single protein at a time. This is a very time-consuming process since it can take years to purify and identify a protein based on its biochemical activity. The availability of an entire genome sequence makes it possible to perform biochemical assays on every protein encoded by the genome.

To this end, it would be useful to analyze hundreds or thousands of protein samples using a single protein chip. Such approaches lend themselves well to high throughput experiments in which large amounts of data can be generated and analyzed. Microtiter plates containing 96 or 384 wells have been known in the field for many years. However, the size (at least 12.8 cm×8.6 cm) of these plates makes them unsuitable for the large-scale analysis of proteins because the density of wells is not high enough.

As noted above, other types of arrays have been devised for use in DNA synthesis and hybridization reactions, e.g., as described in WO 89/10977. However, these arrays are unsuitable for protein analysis in discrete volumes because the arrays are constructed on flat surfaces which tend to become cross-contaminated between features.

Photolithographic techniques have been applied to making a variety of arrays, from oligonucleotide arrays on flat surfaces (Pease et al., 1994, "Light-generated oligonucleotide arrays for rapid DNA sequence analysis," PNAS 91:5022-5026) to arrays of channels (U.S. Pat. No. 5,843,767) to arrays of wells connected by channels (Cohen et al., 1999, "A microchip-based enzyme assay for protein kinase A," Anal Biochem. 273:89-97). Furthermore, microfabrication and microlithography techniques are well known in the semiconductor fabrication area. See, e.g., Moreau, *Semiconductor Lithography: Principals Practices and Materials*, Plenum Press, 1988.

Recently devised methods for expressing large numbers of proteins with potential utility for biochemical genomics in the budding yeast *Saccharomyces cerevisiae* have been developed. ORFs have been cloned into an expression vector that uses the GAL promoter and fuses the protein to a polyhistidine (e.g., HISX6) label. This method has thus far been used to prepare and confirm expression of about 2000 yeast protein fusions (Heyman et al., 1999, "Genome-scale cloning and expression of individual open reading frames using topoisomerase I-mediated ligation," Genome Res. 9:383-392). Using a recombination strategy, about 85% of the yeast ORFs have been cloned in frame with a GST coding region in a vector that contains the CUP1 promoter (inducible by copper), thus producing GST fusion proteins (Martzen et al., 1999, "A biochemical genomics approach for identifying genes by the activity of their products," Science 286:1153-1155). Martzen et al. used a pooling strategy to screen the collection of fusion proteins for several biochemical activities (e.g., phosphodiesterase and Appr-1-P-processing activities) and identified the relevant genes encoding these activities. However, strategies to analyze large numbers of individual protein samples have not been described.

Thus, the need exists for a protein chip in which the wells are densely packed on the chip so as to gain cost and time advantage over the prior art chips and methods.

Citation or identification of any reference in Section II or any other section of this application shall not be considered as admission that such reference is available as prior art to the present invention.

III. SUMMARY OF THE INVENTION

The invention is directed to protein chips, i.e., positionally addressable arrays of proteins on a solid support, useful for the large-scale study of protein function wherein the protein chip contains densely packed reaction wells. The invention is also directed to methods of using protein chips to assay the presence, amount, and/or functionality of proteins present in at least one sample. The invention also is directed to methods of using the protein chips for high density and small volume chemical reactions. Also, the invention is directed to polymers useful as protein chip substrates and methods of making protein chips. The invention is directed to compounds useful for the derivatization of protein chips.

In one embodiment, the present invention provides a protein chip comprising a flat surface, such as, but not limited to, glass slides. Dense protein arrays can be produced on, for example, glass slides, such that chemical reactions and assays can be conducted, thus allowing large-scale parallel analysis of the presence, amount, and/or functionality of proteins. In a specific embodiment, the flat surface array has proteins bound to its surface via a 3-glycidooxypropyltrimethoxysilane (GPTS) linker.

Furthermore, in another specific embodiment, the present invention overcomes the disadvantages and limitations of the methods and apparatus known in the art by providing protein chips with densely packed wells in which chemical reactions and assays can be conducted, thus allowing large-scale parallel analysis of the presence, amount, and/or functionality of proteins.

The general advantages of assaying arrays rather than one-by-one assays include the ability to simultaneously identify many protein-probe interactions, and to determine the relative affinity of these interactions. The advantages of applying complex mixtures of probes to a chip include the ability to detect interactions in a milieu more representative of that in a cell, and the ability to simultaneously evaluate many potential ligands.

In one embodiment, the invention is a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of substances consists of at least 100 different substances per $cm^2$.

In another embodiment, the invention is a positionally addressable array comprising a plurality of different proteins, or molecules comprising functional domains of said proteins, on a solid support, with each different protein or molecule being at a different position on the solid support, wherein the plurality of different proteins or molecules consists of at least 50% of all expressed proteins with the same type of biological activity in the genome of an organism.

In yet another embodiment, the invention is a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the solid support is selected from the group consisting of ceramics, amorphous silicon carbide, castable oxides, polyimides, polymethylmethacrylates, polystyrenes and silicone elastomers.

In still another embodiment, the invention is a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of different substances are attached to the solid support via a 3-glycidooxypropyltrimethoxysilane linker.

In another embodiment, the invention is an array comprising a plurality of wells on the surface of a solid support wherein the density of the wells is at least 100 wells/$cm^2$.

The present invention also relates to a method of making a positionally addressable array comprising a plurality of wells on the surface of a solid support comprising the step of casting an array from a microfabricated mold designed to produce a density of greater than 100 wells/cm on a solid surface. In another embodiment, the invention is a method of making a positionally addressable array comprising a plurality of wells on the surface of a solid support comprising the steps of casting a secondary mold from a microfabricated mold designed to produce a density of wells on a solid surface of greater than 100 wells/$cm^2$ and casting at least one array from the secondary mold.

In yet another embodiment, the invention is a method of using a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of different substances consists of at least 100 different substances per $cm^2$, comprising the steps of contacting a probe with the array, and detecting protein/probe interaction.

In still another embodiment, the invention is a method of using a positionally addressable array comprising a plurality of different proteins, or molecules comprising functional domains of said proteins, on a solid support, with each different protein or molecule being at a different position on the solid support, wherein the plurality of proteins and molecules consists of at least 50% of all expressed proteins with the same type of biological activity in the genome of an organism, comprising the steps of contacting a probe with the array, and detecting protein/probe interaction.

In another embodiment, the invention is a method of using a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the solid support is selected from the group consisting of ceramics, amorphous silicon carbide, castable oxides, polyimides, polymethylmethacrylates, polystyrenes and silicone elastomers, comprising the steps of contacting a probe with the array, and detecting protein/probe interaction.

In yet another embodiment, the invention is a method of using a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of different substances are attached to the solid support via a 3-glycidooxypropyltrimethoxysilane linker, comprising the steps of contacting a probe with the array, and detecting protein/probe interaction.

In still another embodiment, the invention is a method of using a positionally addressable array comprising the steps of depositing a plurality of different substances, selected from the group consisting of proteins, molecules comprising functional domains of said proteins, whole cells, and protein-containing cellular material, on a solid support, with each different substance being at a different position on the solid support, wherein the plurality of different substances consists of at least 100 different substances per $cm^2$, contacting a probe with the array, and detecting protein/probe interaction.

In a specific embodiment, the invention is a method of using a positionally addressable array comprising the steps of depositing a plurality of different substances, selected from the group consisting of proteins, molecules comprising functional domains of said proteins, whole cells, and protein-containing cellular material, on a solid support, with each different substance being at a different position on the solid support, wherein the plurality of different substances consists of at least 100 different substances per $cm^2$, and wherein the solid support is a glass slide, contacting a probe with the array, and detecting protein/probe interaction. In another embodiment, the invention is a method of using a positionally addressable array comprising the steps of depositing a plurality of different proteins, or molecules comprising functional domains of said proteins, on a solid support, with each different protein or molecule being at a different position on the solid support, wherein the plurality of different proteins or molecules consists of at least 50% of all expressed proteins with the same type of biological activity in the genome of an organism, contacting a probe with the array, and detecting protein/probe interaction.

In another embodiment, the invention is a method of using a positionally addressable array comprising the steps of depositing a plurality of different proteins, or molecules comprising functional domains of said proteins, on a solid support, with each different protein or molecule being at a different position on the solid support, wherein the plurality of different proteins or molecules consists of at least 50% of all expressed proteins with the same type of biological activity in the genome of an organism, and wherein the solid support is a glass slide, contacting a probe with the array, and detecting protein/probe interaction.

In another embodiment, the invention is a method of making a positionally addressable array comprising the steps of casting an array from a microfabricated mold designed to produce a density of wells on a solid surface of greater than 100 wells/cm$^2$ and depositing in the wells a plurality of different substances, selected from the group consisting of proteins, molecules comprising functional domains of said proteins, whole cells, and protein-containing cellular material, on a solid support, with each different substances being in a different well on the solid support.

In another embodiment, the invention is a method of making a positionally addressable array comprising the steps of casting a secondary mold from a microfabricated mold designed to produce a density of wells on a solid surface of greater than 100 wells/cm$^2$, casting at least one array from the secondary mold, and depositing in the wells a plurality of different substances, selected from the group consisting of proteins, molecules comprising functional domains of said proteins, whole cells, and protein-containing cellular material, not attached to a solid support, with each different substances being in a different well.

In yet another embodiment, the invention is a method of making a positionally addressable array comprising the steps of casting a secondary mold from a microfabricated mold designed to produce a density of wells on a solid surface of greater than 100 wells/cm$^2$, casting at least one array from the secondary mold, and depositing in the wells a plurality of different substances, selected from the group consisting of proteins, molecules comprising functional domains of said proteins, whole cells, and protein-containing cellular material, with each different substance being in a different well.

A. DEFINITIONS

As used in this application, "protein" refers to a full-length protein, portion of a protein, or peptide. Proteins can be prepared from recombinant overexpression in an organism, preferably bacteria, yeast, insect cells or mammalian cells, or produced via fragmentation of larger proteins, or chemically synthesized.

As used in this application, "functional domain" is a domain of a protein which is necessary and sufficient to give a desired functional activity. Examples of functional domains include, inter alia, domains which exhibit kinase, protease, phosphatase, glycosidase, acetylase, transferase, or other enzymatic activity. Other examples of functional domains include those domains which exhibit binding activity towards DNA, RNA, protein, hormone, ligand or antigen.

As used in this application, "probe" refers to any chemical reagent which binds to a nucleic acid (e.g., DNA or RNA) or protein. Examples of probes include, inter alia, other proteins, peptides, oligonucleotides, polynucleotides, DNA, RNA, small molecule substrates and inhibitors, drug candidates, receptors, antigens, hormones, steroids, phospholipids, antibodies, cofactors, cytokines, glutathione, immunoglobulin domains, carbohydrates, maltose, nickel, dihydrotrypsin, and biotin.

Each protein or probe on a chip is preferably located at a known, predetermined position on the solid support such that the identity of each protein or probe can be determined from its position on the solid support. Further, the proteins and probes form a positionally addressable array on a solid support.

IV. BRIEF DESCRIPTION OF THE DRAWINGS

FIG. 1a. Using the depicted recombination strategy, 119 yeast protein kinases were cloned in a high copy URA3 expression vector (pEGKG) that produces GST fusion proteins under the control of the galactose-inducible GAL10 promoter. GST::kinase constructs were rescued into E. coli, and sequences at the 5'-end of each construct were determined. The whole procedure was repeated when mutations were discovered.

Figure 1B:
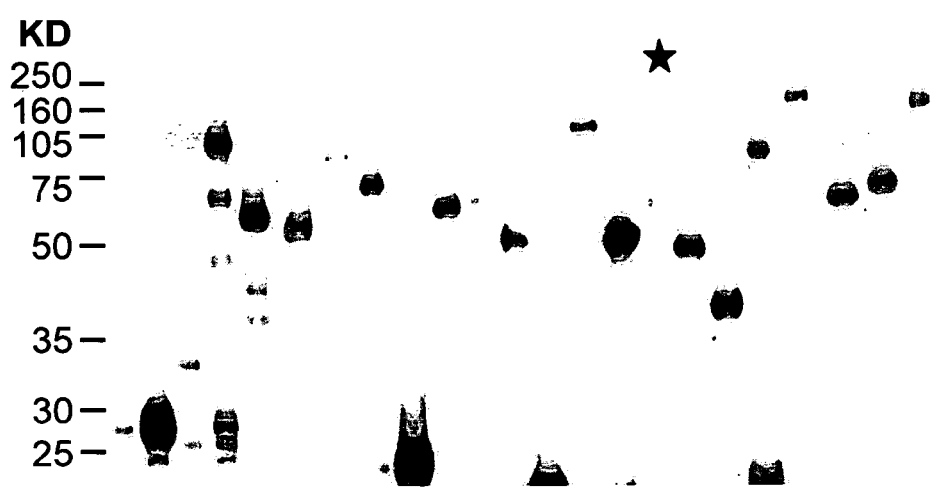

FIG. 1b. Immunoblots of GST::kinase fusion proteins purified as described. From three attempts, 106 kinase proteins were purified. In spite of repeated attempts, the last 14 of 119 GST fusions were undetectable by immunoblotting analysis, (e.g., Mps1 in the lane labeled with star).

Figure 2A:
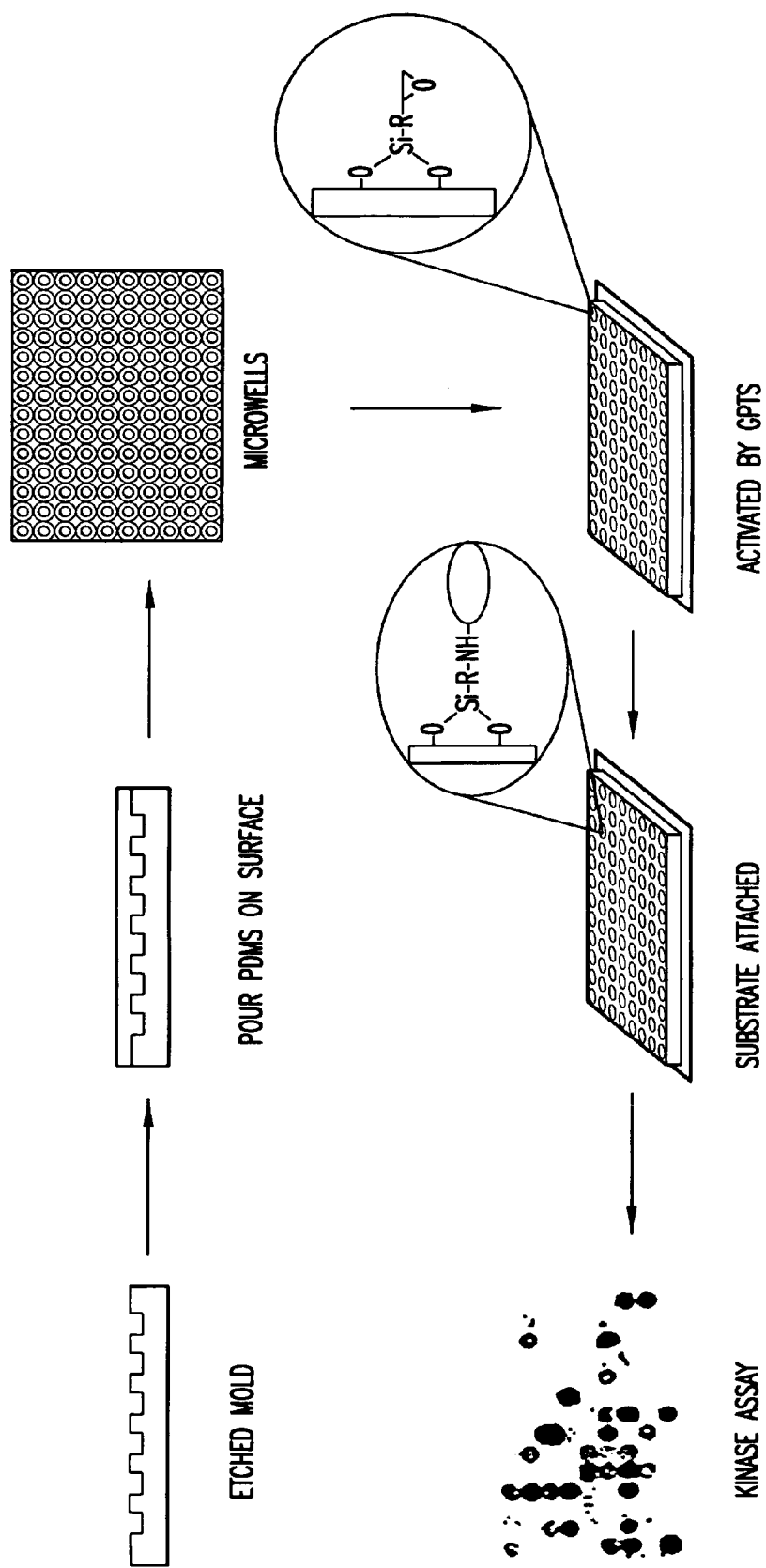

FIG. 2a. The protein chips used in the kinase study were produced according to the following process, schematically depicted. The polydimethylsiloxane (PDMS) was poured over an acrylic master mold. After curing, the chip containing the wells was peeled away and mounted on a glass slide. Next, the surface of the chip was derivatized and proteins were then attached to the wells. Wells were first blocked with 1% BSA, after which kinase, $^{33}$P-γ-ATP, and buffer were added. After incubation for 30 minutes at 30° C., the protein chips were washed extensively, and exposed to both X-ray film and a Molecular Dynamics PhosphorImager, which has a resolution of 50 μm and is quantitative. For twelve substrates, each kinase assay was repeated at least twice; for the remaining five substrates, the assays were performed once.

Figure 2B:
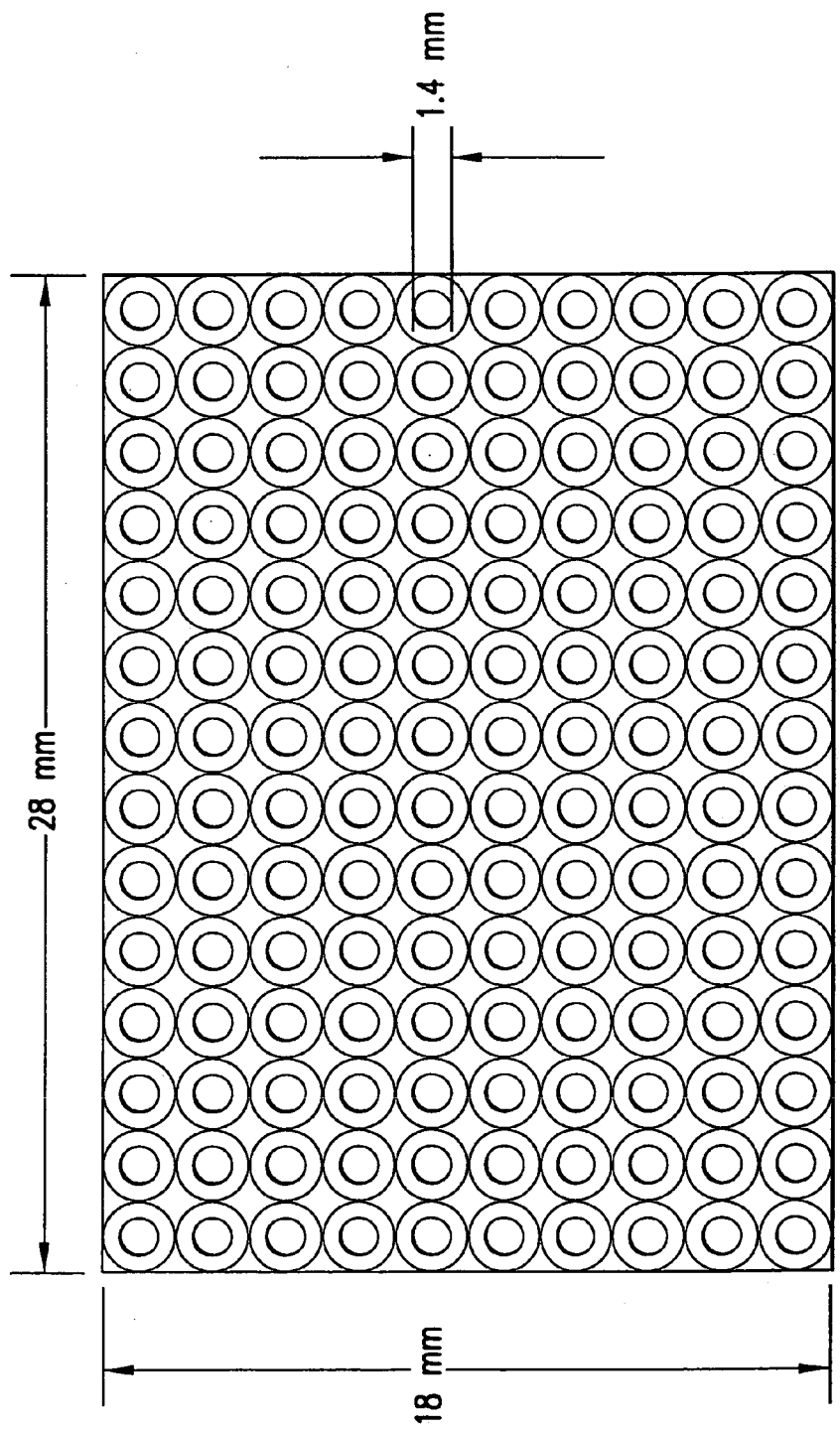

FIG. 2b. An enlarged picture of a protein chip.

FIG. 3. Protein chip and kinase assay results. Position 19 on every chip indicates the signal of negative control. Mps1 at position B4 showed strong kinase activities in all 12 kinase reactions, although no visible signal could be detected on a western blot (FIG. 1b).

FIG. 4a. Quantitative analysis of protein kinase reactions. Kinase activities were determined using a Molecular Dynamics PhosphorImager, and the data were exported into an Excel spreadsheet. The kinase signals were then transformed into fold increases by normalizing the data against negative control. Signals of 119 kinases in four reactions are shown in log scale. The fold increases ranges from 1 to 1000 fold.

FIG. 4b. To determine substrate specificity, specificity index (SI) was calculated using the following formula: $SI_{ir}=F_{ir}/[(F_{i1}+F_{i2}+\ldots+F_{ir})/r]$, where i represents the identity of the kinase used, r represents the identity of the substrate, and $F_{ir}$ represents the fold increase of a kinase i on substrate r compared with GST alone. Several examples of kinase specificity are shown when SI is greater than three.

Figure 5A:
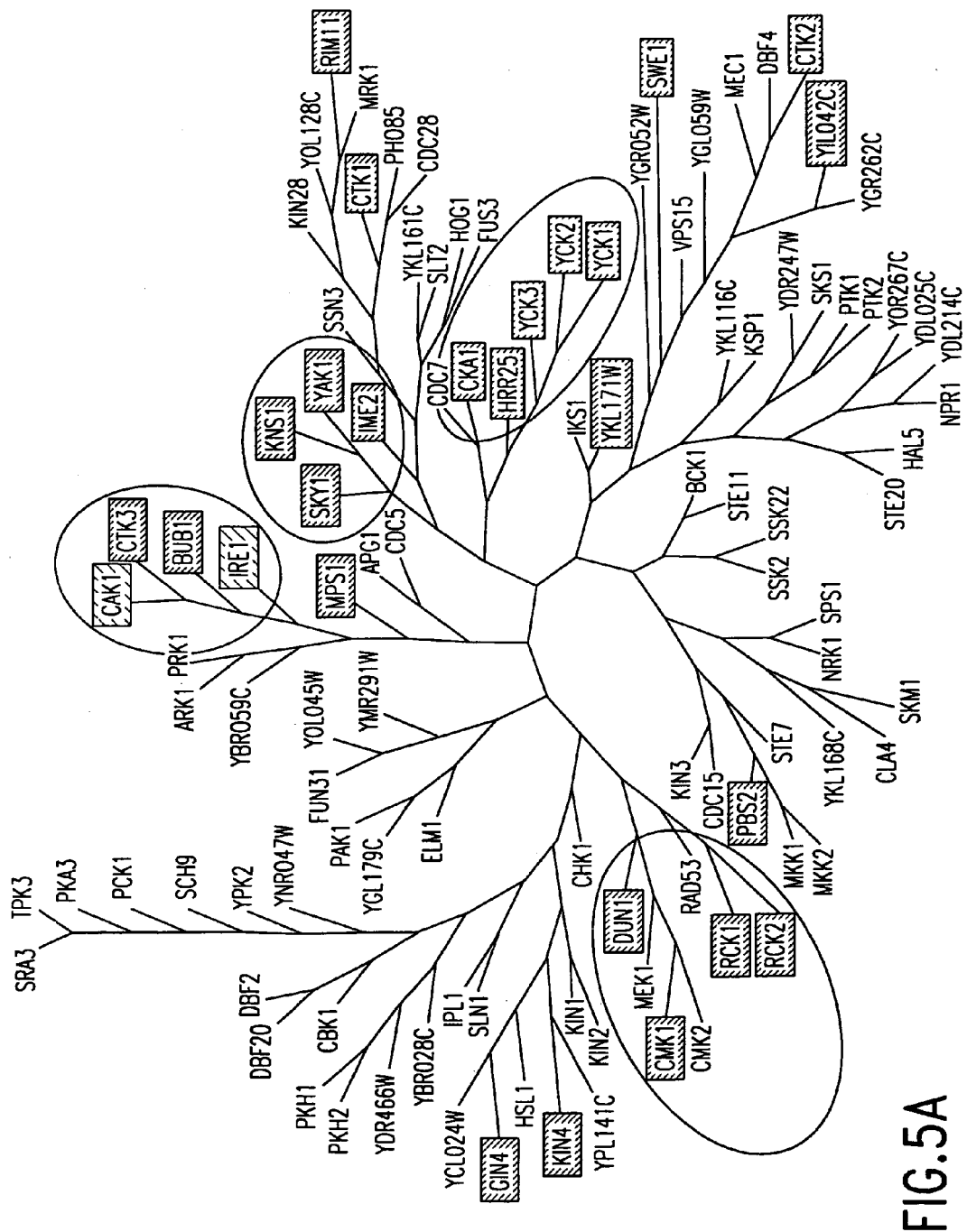

FIG. 5a. Phylogenetic tree derived from the kinase core domain multiple sequence alignment, illustrating the correlation between functional specificity and amino sequences of the poly(Tyr-Glu) kinases. Kinases that can use poly(Thr-Glu) as a substrate often map to specific regions on a sequence comparison dendrogram. The kinases that efficiently phosphorylate poly(Tyr-Glu) are indicated by shading; two kinases that weakly use this substrate are indicated in boxes. Rad53 and Ste7, which could not phosphorylate poly(Tyr-Glu), are indicated by asterisks. As shown, 70% of these kinases lie in four sequence groups (circled).

Figure 5B:
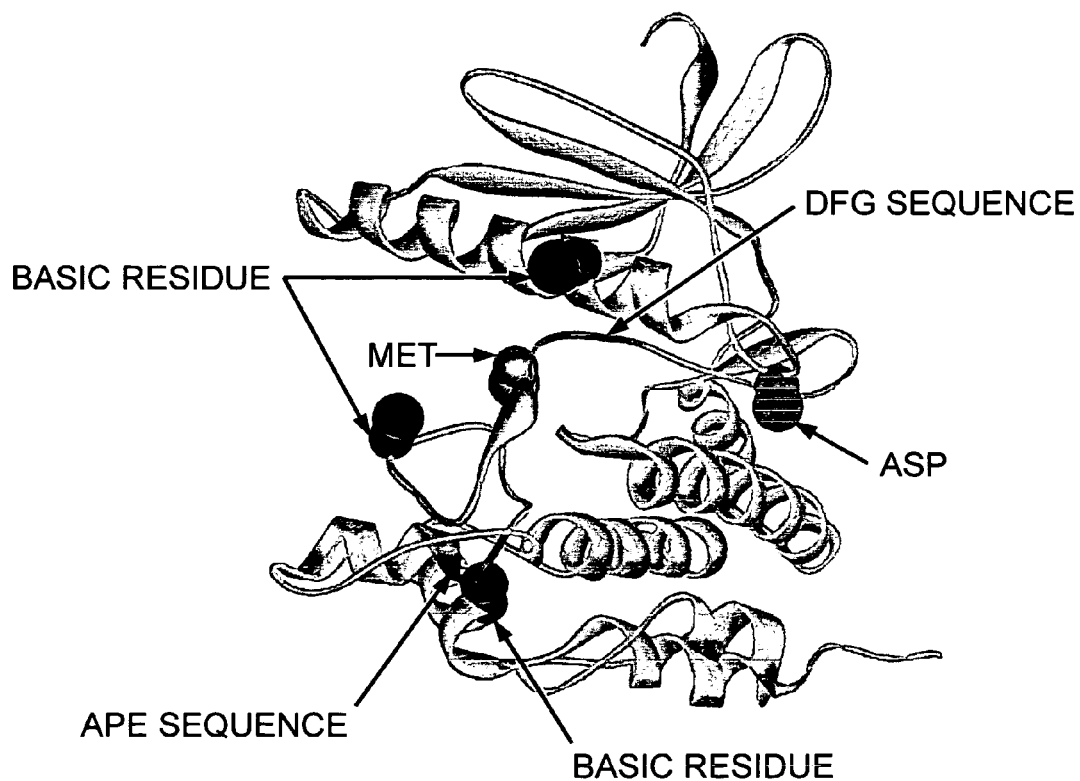

FIG. 5b. Structure of the rabbit muscle phosphorylase kinase (PHK)28. The positions of three basic residues and a methionine (Met) residue, which are preferentially found in kinases that can use poly(Tyr-Glu) as a substrate, are indicated. The asparagine (Asp) residue is usually found in kinases that do not use poly(Tyr-Glu).

FIG. 6. Cross sectional views of lithographic steps in a process of making protein chips.
  a. A silicon wafer with two layers of silicon on either side of an oxide layer.
  b. The silicon wafer with a resistant mask layer on top.
  c. The etching process removes silicon where the surface is unprotected by the resistant mask. The depth of the etching is controlled by the position of the oxide layer, i.e., the etching process does not remove the oxide layer.
  d. The mask layer is removed, leaving the etched silicon wafer.
  e. The protein chip material is applied to the mold.
  f. After curing, the protein chip is removed from the mold. The protein chip has an image that is the negative of the mold.

Figure 7:
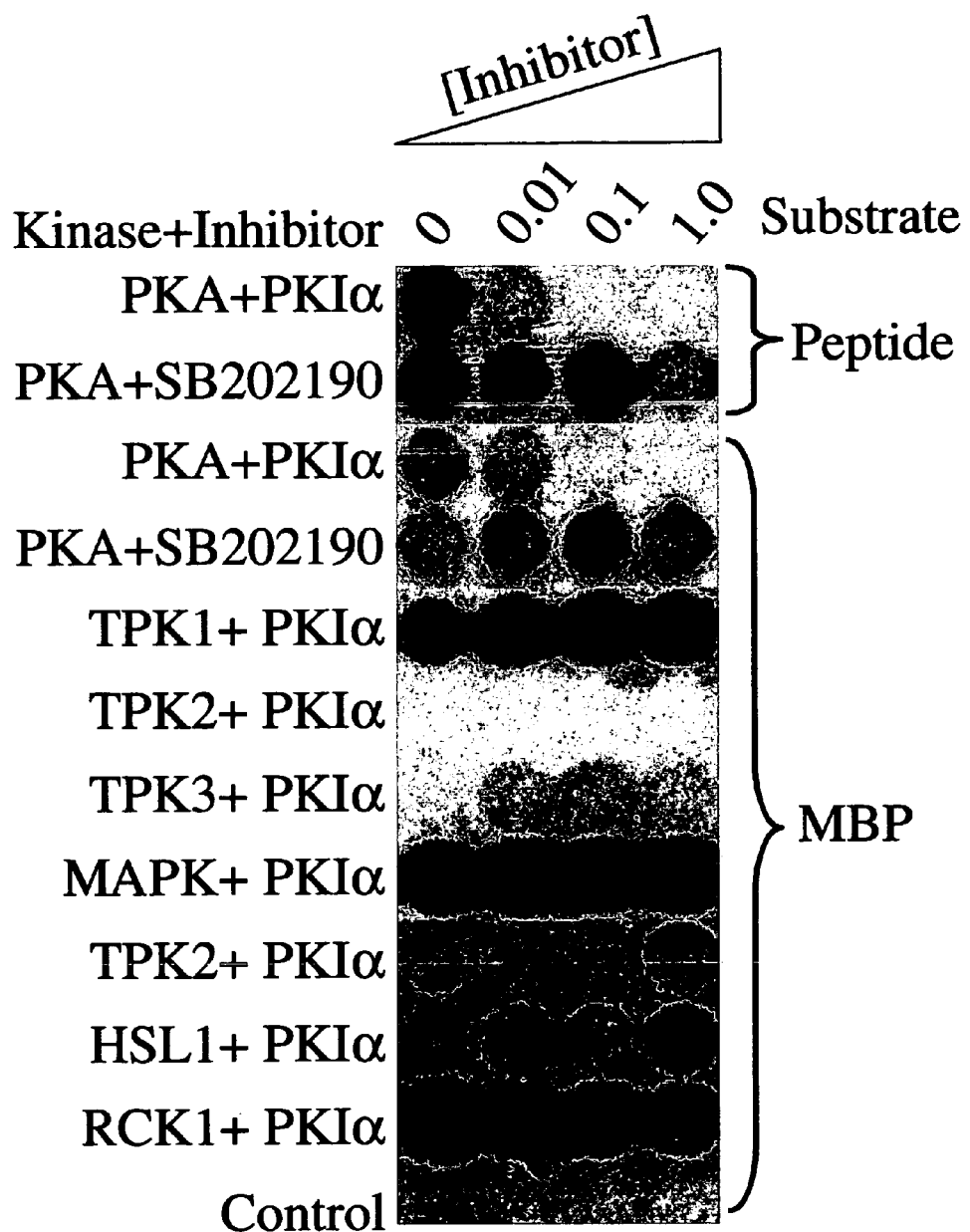

FIG. 7. Kinase/inhibitor assays on a protein chip. A human protein kinase A (PKA), a human map kinase (MAPK), three yeast PKA homologs (TPK1, TPK2 and TPK3), and two other yeast protein kinases (HSL1 and RCK1) were tested against two substrates (i.e., a protein substrate for PKA and a commonly used kinase substrate, MBP) using different concentrations of a specific human PKA inhibitor, PKIα, or a MAPK inhibitor, SB202190. As shown in the figure, PKIα can specifically inhibit PKA activities using both peptide and MBP as substrates. However, SB202190 did not show any inhibitory effect on PKA activity. It is also interesting to note that PKIα did not inhibit the three yeast PKA homologs (TPK1, TPK2, TPK3) or the other two yeast protein kinases tested, HSL1 and RCK1.

V. DETAILED DESCRIPTION OF THE INVENTION

The invention is directed to protein chips, i.e., positionally addressable arrays of proteins on a solid support, useful for the large-scale study of protein function, wherein the protein chip contains densely packed reaction wells. A positionally addressable array provides a configuration such that each probe or protein of interest is located at a known, predetermined position on the solid support such that the identity of each probe or protein can be determined from its position on the array. The invention is also directed to methods of using protein chips to assay the presence, amount, and/or functionality of proteins present in at least one sample. The invention also is directed to methods of using the protein chips for high density and small volume chemical reactions. Also, the invention is directed to polymers useful as protein chip substrates and methods of making protein chips. The invention further relates to compounds useful for the derivatization of protein chip substrate.

In one embodiment, the invention is a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of different substances consists of at least 100 different substances per $cm^2$. In one embodiment, said plurality of different substances consists of between 100 and 1000 different substances per $cm^2$. In another embodiment, said plurality of different substances consists of between 1000 and 10,000 different substances per $cm^2$. In another embodiment, said plurality of different substances consists of between 10,000 and 100,000 different substances per $cm^2$. In yet another embodiment, said plurality of different substances consists of between 100,000 and 1,000,000 different substances per $cm^2$. In yet another embodiment, said plurality of different substances consists of between 1,000,000 and 10,000,000 different substances per $cm^2$. In yet another embodiment, said plurality of different substances consists of between 10,000,000 and 25,000,000 different substances per $cm^2$. In yet another embodiment, said plurality of different substances consists of at least 25,000,000 different substances per $cm^2$. In yet another embodiment, said plurality of different substances consists of at least 10,000,000,000 different substances per $cm^2$. In yet another embodiment, said plurality of different substances consists of at least 10,000,000,000,000 different substances per $cm^2$.

In another embodiment, the invention is a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of different substances consists of at least 100 different substances per $cm^2$, and wherein the solid support is a glass slide.

In another embodiment, the invention is a positionally addressable array comprising a plurality of different substances, selected from the group consisting of proteins, molecules comprising functional domains of said proteins, whole cells, and protein-containing cellular material, on a solid support, with each different substance being at a different position on the solid support, wherein the plurality of different substances consists of about 30 to 100 different substances per $cm^2$. In a specific embodiment, said plurality of different substances consists of 30 different substances per $cm^2$. In a particular embodiment, said plurality of different substances consists of between 30 and 50 different substances per $cm^2$. In another particular embodiment, said plurality of different substances consists of between 50 and 100 different substances per $cm^2$.

In various specific embodiments, the invention is a positionally addressable array comprising a plurality of different proteins, or molecules comprising functional domains of said proteins, on a solid support, with each different protein or molecule being at a different position on the solid support, wherein the plurality of different proteins or molecules consists of at least 50%, 75%, 90%, or 95% of all expressed proteins with the same type of biological activity in the genome of an organism. For example, such organism can be eukaryotic or prokaryotic, and is preferably a mammal, a human or non-human animal, primate, mouse, rat, cat, dog, horse, cow, chicken, fungus such as yeast, Drosophila, *C. elegans*, etc. Such type of biological activity of interest can be, but is not limited to, enzymatic activity (e.g., kinase activity, protease activity, phosphatase activity, glycosidase, acetylase activity, and other chemical group transferring enzymatic activity), nucleic acid binding, hormone binding, etc.

A. Production of Protein Chips

The protein chips with densities of wells in an array of the present invention are preferably cast from master molds which have been stamped, milled, or etched using conventional microfabrication or microlithographic techniques. Preferably conventional microlithographic techniques and materials are utilized in the production of the master molds. Once a master mold has been produced, the master mold may then be used directly to mold the protein chips per se. Alternatively, secondary or tertiary molds can be cast from the master mold and the protein chips cast from these secondary or tertiary molds.

The master mold can be made from any material that is suitable for microfabrication or microlithography, with silicon, glass, quartz, polyimides, and polymethylmethacrylate (Lucite) being preferred. For microlithography, the preferred material is silicon wafers.

Once the appropriate master, secondary, or tertiary mold has been produced, the protein chip is cast. The protein chip can be cast in any solid support that is suitable for casting, including either porous or non-porous solid supports. Ceramics, amorphous silicon carbide, castable oxides that produce casts of $SiO_2$ when cured, polyimides, polymethylmethacrylates, and polystyrenes are preferred solid supports, with silicone elastomeric materials being most preferred. Of the silicone elastomeric materials, polydimethylsiloxane (PDMS) is the most preferred solid support. An advantage of silicone elastomeric materials is the ease with which they are removed from the mold due to their flexible nature.

FIG. 6 illustrates an example of one method useful for realizing high-density arrays of wells on protein chips according to this invention. A silicon wafer with an oxide layer sandwiched between layers of silicon is provided (FIG. 6a). Known as silicon-on-insulator or SOI wafers, these wafers are commonly available from wafer supply companies (e.g., Belle Mead Research, Belle Mead, N.J., and Virginia Semiconductor, Fredericksburg, Va.).

Figure 6A:
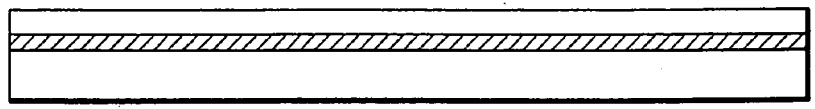
Figure 6B:
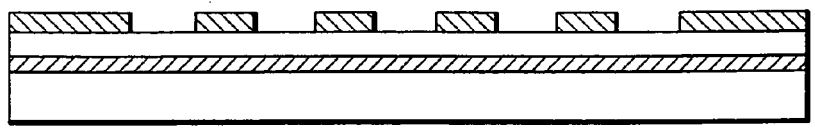
Figure 6C:
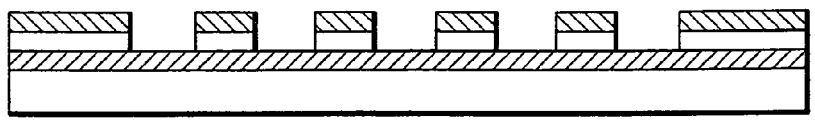
Figure 6D:
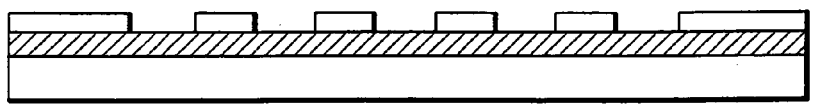

The silicon wafer is then patterned and etched via an etch process (FIGS. 6b-d). The buried oxide layer acts as a very effective etch stop and results in highly uniform etch depth across the wafer. Etch depth is independent of the etch process and merely is determined by the thickness of the top silicon layer.

A wet chemical etch process (e.g., using KOH or tetramethyl hydrazine (TMAH)) can be utilized. However, this technique is slightly more dependent on the crystal orientation of the silicon wafer. Thus, a technique using a rarefied gas (typically $SF_6$) in a reactive ion etch (RIE) is preferred. RIE etching techniques are capable of realizing highly anisotropic wells in silicon that are independent of the crystal orientation of the silicon wafer. The references G. Kovacs, *Micromachined Transducers Sourcebook*, Academic Press (1998) and M. Madou, *Fundamentals of Microfabrication*, CRC Press (1997) provide background on etching techniques.

Both types of microlithography can be utilized on a single chip to obtain the desired combination of well shapes. Wet-chemical etching is an isotropic process which gives U-shaped wells, while RIE is an anisotropic process which gives square bottomed wells.

Figure 6E:
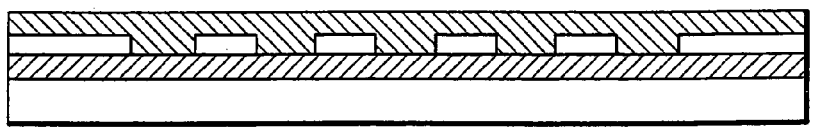
Figure 6F:

After etching the wafer to realize a master mold, it can be used to cast protein chips (FIGS. 6e-f). These structures can be the protein chips or themselves be secondary or tertiary molds from which additional casting of protein chips occurs.

Thus, in one embodiment, a method of making a positionally addressable array, comprising a plurality of wells on the surface of a solid support, comprises casting an array from a microfabricated mold designed to produce a density of wells on a solid surface of greater than 100 wells/cm² In another embodiment, a method of making a positionally addressable array, comprising a plurality of wells on the surface of a solid support, comprises casting a secondary mold from said microfabricated mold designed to produce a density of wells on a solid surface of greater than 100 wells/cm² and casting at least one array from the secondary mold. In yet another embodiment, a method of making a positionally addressable array comprises covering the mold with a liquid cast material, and curing the cast material until the cast is solid. The liquid cast material is preferably silicone elastomer, most preferably polydimethylsiloxane. Into any of these positionally addressable arrays, a plurality of different substances, selected from the group consisting of proteins, molecules comprising functional domains of said proteins, whole cells, and protein-containing cellular material, can be deposited such that each different substance is found in a different well on the solid support.

B. Features of Protein Chips

The protein chips of the present invention are not limited in their physical dimensions and may have any dimensions that are convenient. For the sake of compatibility with current laboratory apparatus, protein chips the size of a standard microscope slide or smaller are preferred. Most preferred are protein chips sized such that two chips fit on a microscope slide. Also preferred are protein chips sized to fit into the sample chamber of a mass spectrometer.

The wells in the protein chips of the present invention may have any shape such as rectangular, square, or oval, with circular being preferred. The wells in the protein chips may have square or round bottoms, V-shaped bottoms, or U-shaped bottoms. Square bottoms are slightly preferred because the preferred reactive ion etch (RIE) process, which is anisotropic, provides square-bottomed wells. The shape of the well bottoms need not be uniform on a particular chip, but may vary as required by the particular assay being carried out on the chip.

The wells in the protein chips of the present invention may have any width-to-depth ratio, with ratios of width-to-depth between about 10:1 and about 1:10 being preferred. The wells in the protein chips of the present invention may have any volume, with wells having volumes of between 1 pl and 5 μl preferred and wells having volumes of between 1 nl and 1 μl being more preferred. The most preferred volume for a well is between 100 nl and 300 nl. For protein chips with very high densities of wells, the preferred volume of a well is between 10 pl and 100 nl.

The protein chips of the invention can have a wide variety of density of wells/cm². The preferred density of wells is between about 25 wells/cm² and about 10,000,000,000,000 wells/cm². Densities of wells on protein chips cast from master molds of laser milled Lucite are generally between 1 well/cm² and 2,500 wells/cm². Appropriate milling tools produce wells as small as 100 μm in diameter and 100 μm apart. Protein chips cast from master mold etched by wet-chemical microlithographic techniques have densities of wells generally between 50 wells/cm² and 10,000,000,000 wells/cm². Wet-chemical etching can produce wells that are 10 μm deep and 10 μm apart, which in turn produces wells that are less than 10 μm in diameter. Protein chips cast from master mold etched by RIE microlithographic techniques have densities of wells generally between 100 wells/cm² and 25,000,000 wells/cm². RIE in combination with optical lithography can produce wells that are 500 nm in diameter and 500 nm apart. Use of electron beam lithography in combination with RIE can produce wells 50 nm in diameter and 50 nm apart. Wells of this size and with equivalent spacing produces protein chips with densities of wells 10,000,000,000,000 wells/cm². Preferably, RIE is used to produce wells of 20 μm in diameter and 20 μm apart. Wells of this size that are equivalently spaced will result in densities of 25,000,000 wells/cm².

The microfabrication and microlithographic techniques described above have been used successfully to wet-chemically etch silicon wafers with well sizes of 560 μm or 280 μm with spacing of about 1 mm. This combination of wells and spacing produces arrays of about 410,000 wells/cm$^2$ and about 610,000 wells/cm$^2$, respectively. When well size and spacing are equivalent, protein chips with about 3.19 million wells/cm$^2$ and 12.75 million wells/cm$^2$ are produced.

In one embodiment, the array comprises a plurality of wells on the surface of a solid support wherein the density of wells is at least 100 wells/cm$^2$. In another embodiment, said density of wells is between 100 and 1000 wells/cm$^2$. In another embodiment, said density of wells is between 1000 and 10,000 wells/cm$^2$. In another embodiment, said density of wells is between 10,000 and 100,000 wells/cm$^2$. In yet another embodiment, said density of wells is between 100,000 and 1,000,000 wells/cm$^2$. In yet another embodiment, said density of wells is between 1,000,000 and 10,000,000 wells/cm$^2$. In yet another embodiment, said density of wells is between 10,000,000 and 25,000,000 wells/cm$^2$. In yet another embodiment, said density of wells is at least 25,000,000 wells/cm$^2$. In yet another embodiment, said density of wells is at least 10,000,000,000 wells/cm$^2$. In yet another embodiment, said density of wells is at least 10,000,000,000,000 wells/cm$^2$.

C. Utilization of Protein Chips

In one embodiment, the present invention provides a protein chip comprising a flat surface, such as, but not limited to, glass slides. Dense protein arrays can be produced on, for example, glass slides, such that chemical reactions and assays can be conducted, thus allowing large-scale parallel analysis of the presence, amount, and/or functionality of proteins (e.g., protein kinases). Proteins or probes are bound covalently or non-covalently to the flat surface of the solid support. The proteins or probes can be bound directly to the flat surface of the solid support, or can be attached to the solid support through a linker molecule or compound. The linker can be any molecule or compound that derivatizes the surface of the solid support to facilitate the attachment of proteins or probes to the surface of the solid support. The linker may covalently or non-covalently bind the proteins or probes to the surface of the solid support. In addition, the linker can be an inorganic or organic molecule. Preferred linkers are compounds with free amines. Most preferred among linkers is 3-glycidooxypropyltrimethoxysilane (GPTS).

In another embodiment, the protein chips of the present invention have several advantages over flat surface arrays. Namely, the use of wells eliminates or reduces the likelihood of cross-contamination with respect to the contents of the wells. Another advantage over flat surfaces is increased signal-to-noise ratios. Wells allow the use of larger volumes of reaction solution in a denser configuration, and therefore greater signal is possible. Furthermore, wells decrease the rate of evaporation of the reaction solution from the chip as compared to flat surface arrays, thus allowing longer reaction times.

Another advantage of wells over flat surfaces is that the use of wells permit association studies using a fixed, limited amount of probe for each well on the chip, whereas the use of flat surfaces usually involves indiscriminate probe application across the whole substrate. When a probe in a mixture of probes has a high affinity, but low specificity, the indiscriminate application of the probe mixture across the substrate will saturate many of the proteins with the high affinity probe. This saturation effectively limits the detection of other probes in the mixture. By using wells, a limited amount of a probe can be applied to individual wells on the chip. Thus, the amount of the probe applied to individual proteins can be controlled, and the probe can be different for different proteins (situated in different wells).

Once a protein chip is produced as described above, it can be used to conduct assays and other chemical reactions. For assays, proteins or probes will generally be placed in the wells. The presence or absence of proteins or probes will be detected by the application of probes or proteins, respectively, to the protein chip. The protein-probe interaction can be visualized using a variety of techniques known in the art, some of which are discussed below.

Proteins useful in this invention can be fusion proteins, in which a defined domain is attached to one of a variety of natural proteins, or can be intact non-fusion proteins.

In another embodiment, protein-containing cellular material, such as but not limited to vesicles, endosomes, subcellular organelles, and membrane fragments, can be placed on the protein chip (e.g., in wells). In another embodiment, a whole cell is placed on the protein chip (e.g., in wells). In a further embodiment, the protein, protein-containing cellular material, or whole cell is attached to the solid support of the protein chip.

The protein can be purified prior to placement on the protein chip or can be purified during placement on the chip via the use of reagents that bind to particular proteins, which have been previously placed on the protein chip. Partially purified protein-containing cellular material or cells can be obtained by standard techniques (e.g., affinity or column chromatography) or by isolating centrifugation samples (e.g., P1 or P2 fractions).

Furthermore, proteins, protein-containing cellular material, or cells can be embedded in artificial or natural membranes prior to or at the time of placement on the protein chip. In another embodiment, proteins, protein-containing cellular material, or cells can be embedded in extracellular matrix component(s) (e.g., collagen or basal lamina) prior to or at the time of placement on the protein chip. The proteins of the invention can be in solution, or bound to the surface of the solid support (e.g., in a well, or on a flat surface), or bound to a substrate (e.g., bead) placed in a well of the solid support.

The placement of proteins or probes in the wells can be accomplished by using any dispensing means, such as bubble jet or ink jet printer heads. A micropipette dispenser is preferred. The placement of proteins or probes can either be conducted manually or the process can be automated through the use of a computer connected to a machine.

Since the wells are self-contained, the proteins or probes need not be attached or bound to the surface of the solid support, but rather the proteins or probes can simply be placed in the wells, or bound to a substrate (e.g., bead) that is placed in the wells. Other substrates include, but are not limited to, nitrocellulose particles, glass beads, plastic beads, magnetic particles, and latex particles. Alternatively, the proteins or probes are bound covalently or non-covalently to the surface of the solid support in the wells. The proteins or probes can be bound directly to the surface of the solid support (in the well), or can be attached to the solid support through a linker molecule or compound. The linker can be any molecule or compound that derivatizes the surface of the solid support to facilitate the attachment of proteins or probes to the surface of the solid support. The linker may covalently bind the proteins or probes to the surface of the solid support or the linker may bind via non-covalent interactions. In addition, the linker can be an inorganic or organic molecule. Preferred linkers are compounds with free amines. Most preferred among linkers is 3-glycidooxypropyltrimethoxysilane (GPTS).

Proteins or probes which are non-covalently bound to the well surface may utilize a variety of molecular interactions to accomplish attachment to the well surface such as, for example, hydrogen bonding, van der Waals bonding, electrostatic, or metal-chelate coordinate bonding. Further, DNA-DNA, DNA-RNA and receptor-ligand interactions are types of interactions that utilize non-covalent binding. Examples of receptor-ligand interactions include interactions between antibodies and antigens, DNA-binding proteins and DNA, enzyme and substrate, avidin (or streptavidin) and biotin (or biotinylated molecules), and interactions between lipid-binding proteins and phospholipid membranes or vesicles. For example, proteins can be expressed with fusion protein domains that have affinities for a substrate that is attached to the surface of the well. Suitable substrates for fusion protein binding include trypsin/anhydrotrypsin, glutathione, immunoglobulin domains, maltose, nickel, or biotin and its derivatives, which bind to bovine pancreatic trypsin inhibitor, glutathione-S-transferase, antigen, maltose binding protein, poly-histidine (e.g., HisX6 tag), and avidin/streptavidin, respectively.

D. Assays on Protein Chips

In one embodiment, the protein chips are used in assays by using standard enzymatic assays that produce chemiluminescence or fluorescence. Detection of various proteins and molecular modifications can be accomplished using, for example, photoluminescence, fluorescence using non-protein substrates, enzymatic color development, mass spectroscopic signature markers, and amplification (e.g., by PCR) of oligonucleotide tags. Thus, protein/probe interaction can be detected by, inter alia, chemiluminescence, fluorescence, radiolabeling, or atomic force microscopy. Probes binding to specific elements in the array can also be identified by direct mass spectrometry. For example, probes released into solution by non-degradative methods, which dissociate the probes from the array elements, can be identified by mass spectrometry (see, e.g., WO 98/59361). In another example, peptides or other compounds released into solution by enzymatic digests of the array elements can be identified by mass spectrometry.

The types of assays fall into several general categories. As a first example, each well on the array is exposed to a single probe whose binding is detected and quantified. The results of these assays are visualized by methods including, but not limited to: 1) using radioactively labeled ligand followed by autoradiography and/or phosphoimager analysis; 2) binding of hapten, which is then detected by a fluorescently labeled or enzymatically labeled antibody or high affinity hapten ligand such as biotin or streptavidin; 3) mass spectrometry; 4) atomic force microscopy; 5) fluorescent polarization methods; 6) rolling circle amplification-detection methods (Hatch et al., 1999, "Rolling circle amplification of DNA immobilized on solid surfaces and its application to multiplex mutation detection", Genet. Anal. 15(2):35-40); 7) competitive PCR (Fini et al., 1999, "Development of a chemiluminescence competitive PCR for the detection and quantification of parvovirus B19 DNA using a microplate luminometer", Clin Chem. 45(9):1391-6; Kruse et al., 1999, "Detection and quantitative measurement of transforming growth factor-betal (TGF-betal) gene expression using a semi-nested competitive PCR assay", Cytokine 11(2):179-85; Guenthner and Hart, 1998, "Quantitative, competitive PCR assay for HIV-1 using a microplate-based detection system", Biotechniques 24(5):810-6); 8) calorimetric procedures; and 9) biological assays, e.g., for virus titers.

As a second example, each well on the array is exposed to multiple probes concurrently, including pooling of probes from several sources, whose binding is detected and quantified. The results of these assays are visualized by methods including, but not limited to: 1) mass spectrometry; 2) atomic force microscopy; 3) infrared red or fluorescently labeled compounds or proteins; 4) amplifiable oligonucleotides, peptides or molecular mass labels; and 5) by stimulation or inhibition of the protein's enzymatic activity. Information is gleaned from mixtures of probes because of the positionally addressable nature of the arrays of the present invention, i.e., through the placement of defined proteins at known positions on the protein chip, information about to what the bound probe binds is known. If so desired, positions on the array that demonstrate binding can then be probed with individual probes to identify the specific interaction of interest.

Useful information also can be obtained, for example, by incubating a protein chip with cell extracts, wherein each well on the chip contains a reaction mix to assay an enzymatic activity of interest, and wherein a plurality of different enzymatic and/or substrate activities are assayed, and thereby identifying and measuring the cellular repertoire of particular enzymatic activities. Similarly, the protein chip can be incubated with whole cells or preparations of plasma membranes to assay, for example, for expression of membrane-associated proteins or molecules, or binding properties of cell surface proteins or molecules. Cells, markers on a cell, or substances secreted by a cell that bind to particular locations on the protein chip can be detected using techniques known in the art. For example, protein chips containing arrays of antigens can be screened with B-cells or T-cells, wherein the antigens are selected from the group consisting of synthetic antigens, tissue-specific antigens, disease-specific antigens, antigens of pathogens, and antigens of autologous tissues. The antigen or antigenic determinant recognized by the lymphocytes can be determined by establishing at what position on the array activation of the cells by antigen occurs. Lymphocyte activation can be assayed by various means including, but not limited to, detecting antibody synthesis, detecting or measuring incorporation of $^3$H-thymidine, probing of cell surface molecules with labeled antibodies to identify molecules induced or suppressed by antigen recognition and activation (e.g., IgD, C3b receptor, IL-2 receptor, transferrin receptor, membrane class II MHC molecules, CD23, CD38, PCA-1 molecules, HLA-DR), and identify expressed and/or secreted cytokines.

In another example, mitogens for a specific cell-type can be determined by incubating the cells with protein chips containing arrays of putative mitogens, comprising the steps of contacting a positionally addressable array with a population of cells; said array comprising a plurality of different substances, selected from the group consisting of proteins, molecules comprising functional domains of said proteins, whole cells, and protein-containing cellular material, on a solid support, with each different substance being at a different position on the solid support, wherein the density of different substances is at least 100 different substances per cm$^2$; and detecting positions on the solid support where mitogenic activity is induced in a cell. Cell division can be assayed by, for example, detecting or measuring incorporation of $^3$H-thymidine by a cell. Cells can be of the same cell type (i.e., a homogeneous population) or can be of different cell types.

In yet another example, cellular uptake and/or processing of proteins on the protein chips can be assayed by, for example, using radioactively labeled protein substrates and measuring either a decrease in radioactive substrate concentration or uptake of radioactive substrate by the cells. These assays can be used for either diagnostic or therapeutic purposes. One of ordinary skill in the art can appreciate many appropriate assays for detecting various types of cellular interactions.

Thus, use of several classes of probes (e.g., known mixtures of probes, cellular extracts, subcellular organelles, cell membrane preparations, whole cells, etc.) can provide for large-scale or exhaustive analysis of cellular activities. In particular, one or several screens can form the basis of identifying a "footprint" of the cell type or physiological state of a cell, tissue, organ or system. For example, different cell types (either morphological or functional) can be differentiated by the pattern of cellular activities or expression determined by the protein chip. This approach also can be used to determine, for example, different stages of the cell cycle, disease states, altered physiologic states (e.g., hypoxia), physiological state before or after treatment (e.g., drug treatment), metabolic state, stage of differentiation or development, response to environmental stimuli (e.g., light, heat), cell-cell interactions, cell-specific gene and/or protein expression, and disease-specific gene and/or protein expression.

Enzymatic reactions can be performed and enzymatic activity measured using the protein chips of the present invention. In a specific embodiment, compounds that modulate the enzymatic activity of a protein or proteins on a chip can be identified. For example, changes in the level of enzymatic activity are detected and quantified by incubation of a compound or mixture of compounds with an enzymatic reaction mixture in wells of the protein chip, wherein a signal is produced (e.g., from substrate that becomes fluorescent upon enzymatic activity). Differences between the presence and absence of the compound are noted. Furthermore, the differences in effects of compounds on enzymatic activities of different proteins are readily detected by comparing their relative effect on samples within the protein chips and between chips.

The variety of strategies of using the high density protein chips of the present invention, detailed above, can be used to determine various physical and functional characteristics of proteins. For example, the protein chips can be used to assess the presence and amount of protein present by probing with an antibody. In one embodiment, a polydimethylsiloxane (PDMS) chip of GST fusion proteins can be probed to determine the presence of a protein and/or its level of activity. The protein can be detected using standard detection assays such as luminescence, chemiluminescence, fluorescence or chemifluorescence. For example, a primary antibody to the protein of interest is recognized by a fluorescently labeled secondary antibody, which is then measured with an instrument (e.g., a Molecular Dynamics scanner) that excites the fluorescent product with a light source and detects the subsequent fluorescence. For greater sensitivity, a primary antibody to the protein of interest is recognized by a secondary antibody that is conjugated to an enzyme such as alkaline phosphatase or horseradish peroxidase. In the presence of a luminescent substrate (for chemiluminescence) or a fluorogenic substrate (for chemifluorescence), enzymatic cleavage yields a highly luminescent or fluorescent product which can be detected and quantified by using, for example, a Molecular Dynamics scanner. Alternatively, the signal of a fluorescently labeled secondary antibody can be amplified using an alkaline phosphatase-conjugated or horseradish peroxidase-conjugated tertiary antibody.

Identifying substrates of protein kinases, phosphatases, proteases, glycosidases, acetylases, or other group transferring enzymes can also be conducted on the protein chips of the present invention. For example, a wide variety of different probes are attached to the protein chip and assayed for their ability to act as a substrate for particular enzyme(s), e.g., assayed for their ability to be phosphorylated by protein kinases. Detection methods for kinase activity, include, but are not limited to, the use of radioactive labels, such as $^{33}$P-ATP and $^{35}$S-γ-ATP, or fluorescent antibody probes that bind to phosphoamino acids. For example, whereas incorporation into a protein of radioactively labeled phosphorus indicates kinase activity in one assay, another assay can measure the release of radioactively labeled phosphorus into the media, which indicates phosphatase activity. In another example, protease activity can be detected by identifying, using standard assays (e.g., mass spectrometry, fluorescently labeled antibodies to peptide fragments, or loss of fluorescence signal from a fluorescently tagged substrate), peptide fragments that are produced by protease activity and released into the media. Thus, activity of group-transferring enzymes can be assayed readily using several approaches and many independent means of detection, which would be appreciated by one of ordinary skill in the art.

Protein chips can be used to identify proteins on the chip that have specific activities such as specific kinases, proteases, nucleic acid binding properties, nucleotide hydrolysis, hormone binding and DNA binding. Thus, the chip can be probed with a probe that will indicate the presence of the desired activity. For example, if DNA binding is the activity of interest, the chip containing candidate DNA-binding proteins is probed with DNA.

The search for probes (natural or synthetic) that are protein or nucleic acid ligands for an array of proteins can be carried out in parallel on a protein chip. A probe can be a cell, protein-containing cellular material, protein, oligonucleotide, polynucleotide, DNA, RNA, small molecule substrate, drug candidate, receptor, antigen, steroid, phospholipid, antibody, immunoglobulin domain, glutathione, maltose, nickel, dihydrotrypsin, or biotin. Alternatively, the probe can be an enzyme substrate or inhibitor. For example, the probe can be a substrate or inhibitor of an enzyme chosen from the group consisting of kinases, phosphatases, proteases, glycosidases, acetylases, and other group transferring enzymes. After incubation of proteins on a chip with combinations of nucleic acid or protein probes, the bound nucleic acid or protein probes can be identified by mass spectrometry (Lakey et al., 1998, "Measuring protein-protein interactions", Curr Opin Struct Biol. 8:119-23).

The identity of target proteins from pathogens (e.g., an infectious disease agent such as a virus, bacterium, fungus, or parasite) or target proteins from abnormal cells (e.g., neoplastic cells, diseased cells, or damaged cells) that serve as antigens in the immune response of recovering or non-recovering patients can be determined by using a protein chip of the invention. For example, lymphocytes isolated from a patient can be used to screen protein chips comprising arrays of a pathogen's proteins on a protein chip. In general, these screens comprise contacting a positionally addressable array with a plurality of lymphocytes, said array comprising a plurality of potential antigens on a solid support, with each different antigen being at a different position on the solid support, wherein the density of different antigens is at least 100 different antigens per $cm^2$, and detecting positions on the solid support where lymphocyte activation occurs. In a specific embodiment, lymphocytes are contacted with a pathogen's proteins on an array, after which activation of B-cells or T-cells by an antigen or a mixture of antigens is assayed, thereby identifying target antigens derived from a pathogen.

Alternatively, the protein chips are used to characterize an immune response by, for example, screening arrays of potential antigens to identify the targets of a patient's B-cells and/or T-cells. For example, B-cells can be incubated with an array of potential antigens (i.e., molecules having antigenic determinants) to identify antigenic targets for humoral-based immunity. The source of antigens can be, for example, from autologous tissues, collections of known or unknown antigens (e.g., of pathogenic microorganisms), tissue-specific or disease-specific antigen collections, or synthetic antigens.

In another embodiment, lymphocytes isolated from a patient can be used to screen protein chips comprising arrays of proteins derived from a patient's own tissues. Such screens can identify substrates of autoimmunity or allergy-causing proteins, and thereby diagnose autoimmunity or allergic reactions, and/or identify potential target drug candidates.

In another embodiment, the protein chips of the invention are used to identify substances that are able to activate B-cells or T-cells. For example, lymphocytes are contacted with arrays of test molecules or proteins on a chip, and lymphocyte activation is assayed, thereby identifying substances that have a general ability to activate B-cells or T-cells or subpopulations of lymphocytes (e.g., cytotoxic T-cells).

Induction of B-cell activation by antigen recognition can be assayed by various means including, but not limited to, detecting or measuring antibody synthesis, incorporation of $^{3}$H-thymidine, binding of labeled antibodies to newly expressed or suppressed cell surface molecules, and secretion of factors indicative of B-cell activation (e.g., cytokines). Similarly, T-cell activation in a screen using a protein chip of the invention can be determined by various assays. For example, a chromium ($^{51}$Cr) release assay can detect recognition of antigen and subsequent activation of cytotoxic T-cells (see, e.g., Palladino et al., 1987, Cancer Res. 47:5074-9; Blachere et al., 1993, J. Immunotherapy 14:352-6).

The specificity of an antibody preparation can be determined through the use of a protein chip of the invention, comprising contacting a positionally addressable array with an antibody preparation, said array comprising a plurality of potential antigens on a solid support, with each different antigen being at a different position on the solid support, wherein the density of different antigens is at least 100 different antigens per cm$^2$, and detecting positions on the solid support where binding by an antibody in the antibody preparation occurs. The antibody preparation can be, but is not limited to, Fab fragments, antiserum, and polyclonal, monoclonal, chimeric, single chain, humanized, or synthetic antibodies. For example, an antiserum can be characterized by screening disease-specific, tissue-specific, or other identified collections of antigens, and determining which antigens are recognized. In a specific embodiment, protein chip arrays having similar or related antigens are screened with monoclonal antibodies to evaluate the degree of specificity by determining to which antigens on the array a monoclonal antibody binds.

The identity of targets of specific cellular activities can be assayed by treating a protein chip with complex protein mixtures, such as cell extracts, and determining protein activity. For example, a protein chip containing an array of different kinases can be contacted with a cell extract from cells treated with a compound (e.g., a drug), and assayed for kinase activity. In another example, a protein chip containing an array of different kinases can be contacted with a cell extract from cells at a particular stage of cell differentiation (e.g., pluripotent) or from cells in a particular metabolic state (e.g., mitotic), and assayed for kinase activity. The results obtained from such assays, comparing for example, cells in the presence or absence of a drug, or cells at several differentiation stages, or cells in different metabolic states, can provide information regarding the physiologic changes in the cells between the different conditions.

Alternatively, the identity of targets of specific cellular activities can be assayed by treating a protein chip of the invention, containing many different proteins (e.g., a peptide library), with a complex protein mixture (e.g., such as a cell extract), and assaying for modifications to the proteins on the chip. For example, a protein chip containing an array of different proteins can be contacted with a cell extract from cells treated with a compound (e.g., a drug), and assayed for kinase, protease, glycosidase, actetylase, phosphatase, or other transferase activity, for example. In another example, a protein chip containing an array of different proteins can be contacted with a cell extract from cells at a particular stage of cell differentiation (e.g., pluripotent) or from cells in a particular metabolic state (e.g., mitotic). The results obtained from such assays, comparing for example, cells in the presence or absence of a drug, or cells at several stages of differentiation, or cells in different metabolic states, can provide information regarding the physiologic effect on the cells under these conditions.

The protein chips are useful to identify probes that bind to specific molecules of biologic interest including, but not limited to, receptors for potential ligand molecules, virus receptors, and ligands for orphan receptors.

The protein chips are also useful to detecting DNA binding or RNA binding to proteins on the protein chips, and to determine the binding specificity. In addition, particular classes of RNA-binding or DNA-binding proteins (e.g., zinc-finger proteins) can be studied with the protein chips by screening arrays of these proteins with nucleic acid sequences, and determining binding specificity and binding strength.

The identity of proteins exhibiting differences in function, ligand binding, or enzymatic activity of similar biological entities can be analyzed with the protein chips of the present invention. For example, differences in protein isoforms derived from different alleles are assayed for their activities relative to one another.

The high density protein chips can be used for drug discovery, analysis of the mode of action of a drug, drug specificity, and prediction of drug toxicity. For example, the identity of proteins that bind to a drug, and their relative affinities, can be assayed by incubating the proteins on the chip with a drug or drug candidate under different assay conditions, determining drug specificity by determining where on the array the drug bound, and measuring the amount of drug bound by each different protein. Bioassays in which a biological activity is assayed, rather than binding assays, can alternatively be carried out on the same chip, or on an identical second chip. Thus, these types of assays using the protein chips of the invention are useful for studying drug specificity, predicting potential side effects of drugs, and classifying drugs. Further, protein chips of the invention are suitable for screening complex libraries of drug candidates. Specifically, the proteins on the chip can be incubated with the library of drug candidates, and then the bound components can be identified, e.g., by mass spectrometry, which allows for the simultaneous identification of all library components that bind preferentially to specific subsets of proteins, or bind to several, or all, of the proteins on the chip. Further, the relative affinity of the drug candidates for the different proteins in the array can be determined.

Moreover, the protein chips of the present invention can be probed in the presence of potential inhibitors, catalysts, modulators, or enhancers of a previously observed interaction, enzymatic activity, or biological response. In this manner, for example, blocking of the binding of a drug, or disruption of virus or physiological effectors to specific categories of proteins, can be analyzed by using a protein chip of the present invention.

The protein chips of the invention can be used to determine the effects of a drug on the modification of multiple targets by complex protein mixtures, such as for example, whole cells, cell extracts, or tissue homogenates. The net effect of a drug can be analyzed by screening one or more protein chips with drug-treated cells, tissues, or extracts, which then can provide a "signature" for the drug-treated state, and when compared with the "signature" of the untreated state, can be of predictive value with respect to, for example, potency, toxicity, and side effects. Furthermore, time-dependent effects of a drug can be assayed by, for example, adding the drug to the cell, cell extract, tissue homogenate, or whole organism, and applying the drug-treated cells or extracts to a protein chip at various timepoints of the treatment.

Screening of phage display libraries can be performed by incubating a library with the protein chips of the present invention. Binding of positive clones can be determined by various methods known in the art (e.g., mass spectrometry), thereby identifying clones of interest, after which the DNA encoding the clones of interest can be identified by standard methods (see, e.g., Ames et al., 1995, J. Immunol. Methods 184:177-86; Kettleborough et al., 1994, Eur. J. Immunol. 24:952-8; Persic et al., 1997, Gene 187:9-18). In this manner, the chips are useful to select for cells having surface components that bind to specific proteins on the chip. Alternatively, a phage display library can be attached to the chip, such that a positionally addressable array of the library is created, after which the array can be screened repeatedly with different mixtures of probes.

The invention also provides kits for carrying out the assay regimens of the invention. In a specific embodiment, kits of the invention comprise one or more arrays of the invention. Such kits may further comprise, in one or more containers, reagents useful for assaying biological activity of a protein or molecule, reagents useful for assaying interaction of a probe and a protein or molecule, reagents useful for assaying the biological activity of a protein or molecule having a biological activity of interest, and/or one or more probes, proteins or other molecules. The reagents useful for assaying biological activity of a protein or molecule, or assaying interactions between a probe and a protein or molecule, can be contained in each well or selected wells on the protein chip. Such reagents can be in solution or in solid form. The reagents may include either or both the proteins or molecules and the probes required to perform the assay of interest.

In one embodiment, a kit comprises one or more protein chips (i.e., positionally addressable arrays comprising a plurality of different substances, selected from the group consisting of proteins, molecules comprising functional domains of said proteins, whole cells, and protein-containing cellular material, on a solid support, with each different substance being at a different position on the solid support), wherein the plurality of different substances consists of at least 100 different substances per $cm^2$, and in one or more containers, one or more probes, reagents, or other molecules. The substances of the array can be attached to the surface of wells on the solid support. In another embodiment, the protein chip in the kit can have the protein or probe already attached to the wells of the solid support. In yet another embodiment, the protein chip in the kit can have the reagent(s) or reaction mixture useful for assaying biological activity of a protein or molecule, or assaying interaction of a probe and a protein or molecule, already attached to the wells of the solid support. In yet another embodiment, the reagent(s) is not attached to the wells of the solid support, but is contained in the wells. In yet another embodiment, the reagent(s) is not attached to the wells of the solid support, but is contained in one or more containers, and can be added to the wells of the solid support. In yet another embodiment, the kit further comprises one or more containers holding a solution reaction mixture for assaying biological activity of a protein or molecule. In yet another embodiment, the kit provides a substrate (e.g., beads) to which probes, proteins or molecules of interest, and/or other reagents useful for carrying out one or more assays, can be attached, after which the substrate with attached probes, proteins, or other reagents can be placed into the wells of the chip.

In another embodiment, one or more protein chips in the kit have, attached to the wells of the solid support, proteins with a biological activity of interest. In another embodiment, one or more protein chips in the kit have, attached to the wells of the solid support, at least 50%, 75%, 90% or 95% of all expressed proteins with the same type of biological activity in the genome of an organism. In a specific embodiment, one or more protein chips in the kit have, attached to the wells of the solid support, at least 50%, 75%, 90% or 95% of all expressed kinases, phosphatases, glycosidase, proteases, acetylases, other group transferring enzymes, nucleic acid binding proteins, hormone-binding proteins or DNA-binding proteins, within the genome of an organism (e.g., of a particular species).

E. Proteins Useful with the Protein Chips

Full-length proteins, portions of full-length proteins, and peptides whether prepared from recombinant overexpression in an organism, produced via fragmentation of larger proteins, or chemically synthesized, are utilized in this invention to form the protein chip. Organisms whose proteins are overexpressed include, but are not limited to, bacteria, yeast, insects, humans, and non-human mammals such as mice, rats, cats, dogs, pigs, cows and horses. Further, fusion proteins in which a defined domain is attached to one of a variety of natural or synthetic proteins can be utilized. Proteins used in this invention can be purified prior to being attached to, or deposited into, the wells of the protein chip, or purified during attachment via the use of reagents which have been previously attached to, or deposited into, the wells of the protein chip. These reagents include those that specifically bind proteins in general, or bind to a particular group of proteins. Proteins can be embedded in artificial or natural membranes (e.g., liposomes, membrane vesicles) prior to, or at the time of attachment to the protein chip. Alternatively, the proteins can be delivered into the wells of the protein chip.

Proteins used in the protein chips of the present invention are preferably expressed by methods known in the art. The InsectSelect system from Invitrogen (Carlsbad, Calif., catalog no. K800-01), a non-lytic, single-vector insect expression system that simplifies expression of high-quality proteins and eliminates the need to generate and amplify virus stocks, is a preferred expression system. The preferred vector in this system is pIB/V5-His TOPO TA vector (catalog no. K890-20). Polymerase chain reaction (PCR) products can be cloned directly into this vector, using the protocols described by the manufacturer, and the proteins are then expressed with N-terminal histidine (His) labels which can be used to purify the expressed protein.

The BAC-TO-BAC™ system, another eukaryotic expression system in insect cells, available from Lifetech (Rockville, Md.), is also a preferred expression system. Rather than using homologous recombination, the BAC-TO-BAC™ system generates recombinant baculovirus by relying on site-specific transposition in *E. coli*. Gene expression is driven by the highly active polyhedrin promoter, and therefore can represent up to 25% of the cellular protein in infected insect cells.

VI. EXAMPLE I

Analysis of Yeast Protein Kinases Using Protein Chips

A. Introduction

The following example exemplifies the various aspects of protein chip production and a method of using the protein chips of the present invention. The protein chip technology of the present invention is suitable for rapidly analyzing large numbers of samples, and therefore this approach was applied to the analysis of nearly all yeast protein kinases. Protein kinases catalyze protein phosphorylation and play a pivotal role in regulating basic cellular functions, such as cell cycle control, signal transduction, DNA replication, gene transcription, protein translation, and energy metabolism[7]. The availability of a complete genome sequence makes it possible to analyze all of the protein kinases encoded by an organism and determine their in vitro substrates.

The yeast genome has been sequenced and contains approximately 6200 open reading frames greater than 100 codons in length; 122 of these are predicted to encode protein kinases. Twenty-four of these protein kinase genes have not been studied previously[8]. Except for two histidine protein kinases, all of the yeast protein kinases are members of the Ser/Thr family; tyrosine kinase family members do not exist although seven protein kinases that phosphorylate serine/threonine and tyrosine have been reported[8].

With the development of the protein chip technology of the present invention, the high throughput analysis of the biochemical activities of nearly all of the protein kinases from *Saccharomyces cerevisiae* has been conducted as described herein. Protein chips utilized were disposable arrays of 300 nl wells in silicone elastomer sheets placed on top of microscope slides. The high density and small size of the wells allows for high throughput batch processing and simultaneous analysis of many individual samples, requiring only small amounts of protein. Using protein chips of the present invention, *Saccharomyces cerevisiae* kinase proteins (119 different kinases in total) were fused to glutathione-S-transferase (GST), overexpressed in yeast, then purified and assayed for their ability to phosphorylate 17 different substrates. Nearly all of the kinases tested (93%) exhibited activities that were at least five-fold higher than controls, on one or more substrates, including 18 of 24 previously uncharacterized kinases. Thirty-two kinases exhibited preferential phosphorylation of one or two substrates. Twenty-seven kinases readily phosphorylated poly(Tyr-Glu). Since only five of these kinases were previously classified as dual function kinases (i.e., they phosphorylate both Ser/Thr and Tyr), these findings greatly expand our knowledge as to which kinases are able to phosphorylate tyrosine residues. Interestingly, these dual specificity kinases often share common amino acid resides that lie near the catalytic region. These results indicate that the protein chip technology of the present invention is useful for high throughput screening of protein biochemical activity, and for the analysis of entire proteomes.

B. Methods

1. Cell Culture, Constructs and Protein Purification

Using the recombination strategy of Hudson et al.[9], 119 of 122 yeast protein kinase genes were cloned into a high copy URA3 expression vector (pEG(KG)), which produces GST fusion proteins under the control of the galactose-inducible GAL10 promoter[10]. Briefly, primers complementary to the end of each ORF were purchased from Research Genetics; the ends of these primers contain a common 20 bp sequence. In a second round of PCR, the ends of these products were modified by adding sequences that are homologous to the vector. The PCR products containing the vector sequences at their ends were transformed along with the vector into a pep4 yeast strain (which lacks several yeast proteases)[10], and Ura+ colonies were selected. Plasmids were rescued in *E. coli*, verified by restriction enzyme digestion and the DNA sequence spanning the vector-insert junction was determined using a primer complementary to the vector. For the GST::Cla4 construct, a frame-shift mutation was found in a poly(A) stretch in the amino terminal coding region. Three independent clones were required to find the correct one that maintained reading frame. For five of these genes, two overlapping PCR products were obtained and introduced into yeast cells. Confirmed plasmids were reintroduced into the pep4 yeast strain for kinase protein purification.

For preparing samples using the 96 well format, 0.75 ml of cells were grown in medium containing raffinose to O.D. (600) about 0.5 in boxes containing 2 ml wells; two wells were used for each strain. Galactose was added to a final concentration of 4% to induce protein expression, and the cells were incubated for 4 hrs. The cultures of the same strain were combined, washed once with 500 μl of lysis buffer, resuspended in 200 μl of lysis buffer, and transferred into a 96×0.5 ml plate (Dot Scientific, USA) containing 100 μl chilled glass beads. Cells were lysed in the box by repeated vortexing at 4° C. and the GST fusion proteins were purified from these strains using glutathione beads and standard protocols[20] in a 96 well format. The purity of five purified GST::kinase proteins (Swe1, Ptk2, Pkh1, Hog1, Pbs2) was determined by comparing the Coomasie staining patterns of the purified proteins with the patterns obtained by immunoblot analysis using anti-GST antibodies. The results indicated that the purified proteins were more than 90% pure. To purify the activated form of Hog1, the cells were challenged with 0.4 M NaCl in the last five minutes of the induction. Protein kinase activity was stable for at least two months at −70° C. with little or no loss of kinase activity.

2. Chip Fabrication and Protein Attachment

Chips were made from the silicone elastomer, polydimethylsiloxane (PDMS) (Dow Chemical, USA), which was cast over microfabricated molds. Liquid PDMS was poured over the molds and, after curing (at least 4 hours at 65° C.), flexible silicone elastomer array sheets were then peeled from the reusable molds. Although PDMS can be readily cast over microlithographically fabricated structures, for the purposes of the kinase assay described herein, molds made from sheets of acrylic patterned with a computer-controlled laser milling tool (Universal Laser Systems, USA) sufficed.

Over 30 different arrays were tested. The variables tested were width and depth of the wells (widths ranging from 100 μm to 2.5 mm, depths from 100 μm to 1 mm), spacing between wells (100 μm to 1 mm), configuration (either rectangular arrays or closest packed), and well shape (square versus round). The use of laser milled acrylic molds offered a fast and inexpensive method to realize a large number prototype molds of varying parameters.

To determine the conditions that maximize protein attachment to the wells, PDMS was treated with either 5 M $H_2SO_4$, 10 M NaOH, hydrogen peroxide or a 3-glycidooxypropyltrimethoxysilane linker (GPTS)(Aldrich, USA)[11,12] GPTS treatment resulted in the greatest adsorption of protein to the wells relative to untreated PDMS or PDMS treated other ways. Briefly, after washing with 100% EtOH three times at room temperature, the chips were immersed in 1% GPTS solution (95% EtOH, 16 mM HOAc) with shaking for 1 hr at room temperature. After three washes with 95% EtOH, the chips were cured at 135° C. for 2 hrs under vacuum. Cured chips can be stored in dry Argon for months[12]. To attach proteins to the chips, protein solutions were added to the wells and incubated on ice for 1 to 2 hours. After rinsing with cold HEPES buffer (10 mM HEPES, 100 mM NaCl, pH 7.0) three times, the wells were blocked with 1% BSA in PBS (Sigma, USA) on ice for >1 hr. Because of the use of GPTS, any reagent containing primary amine groups was avoided.

To determine the concentration of proteins that can be linked to the treated PDMS, horseradish peroxidase (HRP) anti-mouse Ig (Amersham, USA) was attached to the chip using serial dilutions of the enzyme. After extensive washing with PBS, the bound antibodies were detected using an enhanced chemiluminescent (ECL) detection method (Amersham, USA). Up to $8\times10^{-9}$ μg/μm$^2$ of protein can be attached to the surface; a minimum $8\times10^{-13}$ μg/μm$^2$ is required for detection by our immunostaining methods.

3. Immunoblotting, Kinase Assay and Data Acquisition

Immunoblot analysis was performed as described[34]. GST:: protein kinases were tested for in vitro kinase activity[13] using $^{33}$P-γ-ATP. In the autophosphorylation assay, the GST::kinases were directly adhered to GPTS-treated PDMS and the in vitro reactions carried out with $^{33}$P-γ-ATP in appropriate buffer. In the substrate reactions, the substrate was adhered to the wells via GPTS, and the wells were washed with HEPES buffer and blocked with 1% BSA, before kinase, $^{33}$P-γ-ATP and buffer were added. The total reaction volume was kept below 0.5 μl per reaction. After incubation for 30 minutes at 30° C., the chips were washed extensively, and exposed to both X-ray film and a Molecular Dynamics PhosphorImager, which has a resolution of 50 μm and is quantitative. For twelve substrates each kinase assay was repeated at least twice; for the remaining five, the assays were performed once.

To determine substrate specificity, specificity index (SI) was calculated using the following formula: $S_{ir}=F_{ir}/[(F_{i1}+F_{i2}+ \ldots +F_{ir})/r]$, where i represents the ID of kinase used, r represents the ID of a substrate, and $F_{ir}$ represents the fold increase of a kinase i on substrate r compared with GST alone.

4. Kinase Sequence Alignments and Phylogenetic Trees

Multiple sequence alignments based on the core kinase catalytic domain subsequences of the 107 protein kinases were generated with the CLUSTAL W algorithm[35], using the Gonnet 250 scoring matrix[36]. Kinase catalytic domain sequences were obtained from the SWISS-PROT[37], PIR[38], and GenBank[39] databases. For those kinases whose catalytic domains are not yet annotated (DBF4/YDR052C and SLN1/YIL147C), probable kinase subsequences were inferred from alignments with other kinase subsequences in the data set with the FASTA algorithm[40,41] using the BLOSUM 50 scoring matrix[42]. Protein subsequences corresponding to the eleven core catalytic subdomains[43] were extracted from the alignments, and the phylogenetic trees were computed with the PROTPARS[44] program (FIG. 5a).

5. Functional Grouping of Protein Chip Data

To visualize the approximate functional relationships between protein kinases relative to the experimental data, kinases were hierarchically ordered based on their ability to phosphorylate the 12 different substrates (data available on the Internet at bioinfo.mbb.yale.-edu/genome/yeast/chip as of Aug. 17, 2000). A profile corresponding to the −/+ activity of the 107 protein kinases to each of the substrates was recorded, with discretized values in [0,1]. Matrices were derived from the pairwise Hamming distances between experimental profiles, and unrooted phylogenies were computed using the Fitch-Margoliash least-squares estimation method[45] as implemented in the FITCH program34 of the PHYLIP software package[44]. In each case, the input order of taxa was randomized to negate any inherent bias in the organization of the data set, and optimal hierarchies were obtained through global rearrangements of the tree structures.

C. Results

1. Yeast Kinase Cloning and Protein Purification

Using a recombination-directed cloning strategy[9], we attempted to clone the entire coding regions of 122 yeast protein kinase genes in a high copy expression vector (pEG (KG)) that produces GST fusion proteins under the control of the galactose-inducible GAL10 promoters (FIG. 1a). GST:: kinase constructs were rescued into E. coli, and sequences at the 5'-end of each construct were determined. Using this strategy, 119 of the 122 yeast protein kinase genes were cloned in-frame. The three kinase genes that were not cloned are very large (4.5-8.3 kb).

The GST:kinase fusion proteins were overproduced in yeast and purified from 50 ml cultures using glutathione beads and standard protocols[11]. For the case of Hog1 the yeast cells were treated with high salt to activate the enzyme in the last five minutes of induction; for the rest of the kinases, synthetic media (URA$^-$/raffinose) was used. Immunoblot analysis of all 119 fusions using anti-GST antibodies revealed that 105 of the yeast strains produced detectable GST::fusion proteins; in most cases the fusions were full length. Up to 1 μg of fusion protein per ml of starting culture was obtained (FIG. 1b). However, 14 of 119 GST::kinase samples were not detected by immunoblotting analysis. Presumably, these proteins are not stably overproduced in the pep4 protease-deficient strain used, or these proteins may form insoluble aggregates that do not purify using our procedures. Although this procedure was successful, purification of GST fusion proteins using 50 ml cultures is a time-consuming process and not applicable for preparing thousands of samples. Therefore, a procedure for growing cells in a 96 well format was developed (see Methods). Using this procedure, 119 GST fusions were prepared and purified in six hours with about two-fold higher yields per ml of starting culture relative to the 50 ml method.

2. Protein Chip Design

Protein chips were developed to conduct high throughput biochemical assays of 119 yeast protein kinases (FIG. 2). These chips consist of an array of wells in a disposable silicone elastomer polydimethylsiloxane (PDMS)[11]. Arrays of wells allow small volumes of different probes to be densely packed on a single chip yet remain physically segregated during subsequent batch processing. Proteins were covalently attached to the wells using a linker 3-glycidooxypropyltrimethoxysilane (GPTS)[12]. Up to $8 \times 10^{-9}$ μg/μm² of protein can be attached to the surface (see Methods).

For the purposes of the protein kinase assays, the protein chip technology was configured to be compatible with standard sample handling and recording equipment. Using radio-isotope labeling ($^{33}$P), the kinase assays described below, and manual loading, a variety of array configurations were tested. The following chips produced the best results: round wells with 1.4 mm diameter and 300 μm deep (approximately 300 nl), in a 10×14 rectangular array configuration with a 1.8 mm pitch. A master mold of twelve of these arrays were produced, and a large number of arrays were repeatedly cast for the protein kinase analysis. Chips were placed atop microscope slides for handling purposes (FIG. 2a); the arrays covered slightly more than one third of a standard microscope slide and two arrays per slide were typically used (FIG. 2b). Although a manual pipette method to place proteins in each well was employed, automated techniques may also be used. In addition, this protein chip configuration may also be used with other labeling methods, such as by using fluorescently labeled antibodies to phosphoproteins, and subsequent detection of immunofluorescence.

3. Large-Scale Kinase Assays Using Protein Chips

All 119 GST::protein kinases were tested for in vitro kinase activity[13] in 17 different assays using $^{33}$P-γ-ATP and 17 different chips. Each chip was assayed using a different substrate, as follows: 1) Autophosphorylation, 2) Bovine Histone H1 (a common kinase substrate), 3) Bovine Casein (a common substrate), 4) Myelin basic protein (a common substrate), 5) Ax12 C terminus-GST (Ax12 is a transmembrane phosphoprotein involved in budding)[14], 6) Rad9 (a phosphoprotein involved in the DNA damage checkpoint)[15], 7) Gic2 (a phosphoprotein involved in budding)[16], 8) Red1 (a meiotic phosphoprotein important for chromosome synapsis)[17], 9) Mek1 (a meiotic protein kinase important for chromosome synapsis)[18], 10) Poly(tyrosine-glutamate 1:4) (poly(Tyr-Glu)); a tyrosine kinase substrate)[19], 111) Ptk2 (a small molecule transport protein)[20], 12) Hsl1 (a protein kinase involved in cell cycle regulation)[21], 13) Swi6 (a phosphotranscription factor involved in G1/S control)[22], 14) Tub4 (a protein involved in microtubule nucleation)[23], 15) Hog1 (a protein kinase involved in osmoregulation)[24], 16) Hog1 (an inactive form of the kinase), and 17) GST (a control). For the autophosphorylation assay, the kinases were directly adhered to the treated PDMS wells and $^{33}$P-γ-ATP was added; for substrate reactions, the substrates were bound to the wells, and then kinases and $^{33}$P-γ-ATP were added. After the reactions were completed, the slides were washed and the phosphorylation signals were acquired and quantified using a high resolution phosphoimager. Examples are shown in FIG. 3. To identify kinase activities, the quantified signals were converted into fold increases relative to GST controls and plotted for further analysis (FIG. 4a).

As shown in FIG. 4a, most (93.3%) kinases exhibited activity five-fold or greater over background for at least one substrate. As expected, Hrr25, Pbs2 and Mek1 phosphorylated their known substrates[25-27], Swi6 (400-fold higher than the GST control), Hog1 (10-fold higher) and Red1 (10-fold higher), respectively. The results of this assay demonstrated that 18 of the 24 predicted protein kinases have not been studied previously phosphorylate one or more substrates, as do several unconventional kinases[8], including the histidine kinases (Sln1, Yil042c) and phospholipid kinases (e.g Mec1).

To determine substrate specificity, the activity of a particular kinase was further normalized against the average of its activity against all substrates. Several examples are shown in FIG. 4b; all the data are available on the Internet at bioinfo.mbb.yale.edu/genome/yeast/chip. Thirty-two kinases exhibited substrate specificity on a particular substrate with specificity index (SI; see Methods) equal or higher than 2, and reciprocally, most substrates are preferentially phosphorylated by a particular protein kinase or set of kinases. For example, the C terminus of Ax12, a protein involved in yeast cell budding, is preferentially phosphorylated by Dbf20, Kin2, Yak1 and Ste20 relative to other protein. Interestingly, previous studies found that Ste20 was localized at the tip of emerging buds similar to Ax12, and a ste20Δ/cla4$^{ts}$ mutant is unable to bud or form fully polarized actin patches or cables[28]. Another example is the phosphoprotein Gic2, which is also involved in budding[16]. Ste20 and Skm1 strongly phosphorylate Gic2 (FIG. 4b). Previous studies suggested that Cdc42 interacts with Gic2, Cla4[29], Ste20 and Skm1. Our results raise the possibility that Cdc42 may function to promote the phosphorylation of Gic2 by recruiting Ste20 and/or Skm1.

4. Yeast Contain Many Dual Specific Kinases

Of particular interest are the dual specificity kinases, i.e., those enzymes that phosphorylate both Ser/Thr and tyrosine. Based on sequence analysis, all but two yeast protein kinases belong to the Ser/Thr family of protein kinases; however, at the time of the study, seven protein kinases (Mps1, Rad53, Swe1, Ime2, Ste7, Hrr25, and Mck1) were reported to be dual specificity kinases[19]. We confirmed that Swe1, Mps1, Ime2, and Hrr25 readily phosphorylate poly(Tyr-Glu), but we did not detect any tyrosine kinase activity for Ste7, Rad53 or Mck1. Mck1 did not show strong activity in any of our assays; however, Ste7 and Rad53 are very active in other assays. Thus, their inability to phosphorylate poly(Tyr-Glu) indicates that they are either very weak tyrosine kinases in general or at least are weak with the poly(Tyr-Glu) substrate. Consistent with the latter possibility, others have found that poly(Tyr-Glu) is a very poor substrate for Rad53 (Ref 19; D. Stern, pers. comm.). Interestingly, we found that 23 other kinases also efficiently use poly(Tyr-Glu) as a substrate, indicating that there are at least 27 kinases in yeast that are capable of acting in vitro as dual specificity kinases. One of these, Rim1, was recently shown to phosphorylate a Tyr residue on its in vivo substrate, Ime2, indicating that it is a bonafide dual specificity kinase[30]. In summary, this experiment roughly tripled the number of kinases capable of acting as dual specificity kinases, and has raised questions about some of those classified as such kinases.

5. Correlation Between Functional Specificity and Amino Sequences of the Poly(Tyr-Glu) Kinases The large-scale analysis of yeast protein kinases allows us to compare the functional relationship of the protein kinases to one another. We found that many of the kinases that phosphorylate poly(Tyr-Glu) are related to one another in their amino acid sequences: 70% of the poly(Tyr-Glu) kinases cluster into distinct four groups on a dendrogram in which the kinases are organized relative to one another based on sequence similarity of their conserved protein kinase domains (FIG. 5a). Further examination of the amino acid sequence reveals four types of amino acids that are preferentially found in the poly(Tyr-Glu) class of kinases relative to the kinases that do not use poly(Tyr-Glu) as a substrate (three are lysines and one is a methionine); one residue (an asparagine) was preferentially located in the kinases that do not readily use poly(Tyr-Glu) as a substrate (FIG. 5b). Most of the residues lie near the catalytic portion of the molecule (FIG. 5b)[31], suggesting that they may play a role in substrate recognition.

D. Discussion

1. Large-Scale Analysis of Protein Kinases

This study employed a novel protein chip technology to characterize the activities of 119 protein kinases for 17 different substrates. We found that particular proteins are preferred substrates for particular protein kinases, and vice versa, many protein kinases prefer particular substrates. One concern with these studies is that it is possible that kinases other than the desired enzyme are contaminating our preparations. Although this cannot be rigorously ruled out, analysis of five of our samples by Coomasie staining and immunoblot staining with anti-GST does not reveal any detectable bands in our preparation that are not GST fusions (see methods).

It is important to note that in vitro assays do not ensure that a substrate for a particular kinase in vitro is phosphorylated by the same kinase in vivo. Instead, these experiments indicate that certain proteins are capable of serving as substrates for specific kinases, thereby allowing further analysis. In this respect, these assays are analogous to two-hybrid studies in which candidate interactions are detected. Further experimentation is necessary to determine if the processes normally occur in vivo.

Consistent with the idea that many of the substrates are likely to be bonafide substrates in vivo is the observation that three kinases, Hrr25, Pbs2 and Mek1, phosphorylate their known substrates in our assays. Furthermore, many of the kinases (e.g., Ste20) co-localize with their in vitro substrates (e.g., Axl2). Thus, we expect many of the kinases that phosphorylate substrates in our in vitro assays are likely also to do so in vivo. Although most of the kinases were active in our assays, several were not. Presumably, our preparations of these latter kinases either lack sufficient quantities of an activator or were not purified under activating conditions. For example, Cdc28 which was not active in our assays, might be lacking its activating cyclins. For the case of Hog1, cells were treated with high salt to activate the enzyme. Since nearly all of our kinase preparations did exhibit activity, we presume that at least some of the enzyme in the preparation has been properly activated and/or contains the necessary cofactors. It is likely that the overexpression of these enzymes in their native organism contributes significantly to the high success of obtaining active enzymes.

Using the assays on the protein chip, many kinases that utilize poly(Tyr-Glu) were identified. The large-scale analysis of many kinases allowed the novel approach of correlating functional specificity of poly(Tyr-Glu) kinases with specific amino acid sequences. Many of the residues of the kinases that phosphorylate poly(Tyr-Glu) contain basic residues. This might be expected if there were electrostatic interactions between the kinases residues and the Glu residues. However, the roles of some of the other residues are not obvious such as the Met residues on the kinases that phosphorylate poly(Tyr-Glu) and the Asn on those that do not. These kinase residues may confer substrate specificity by other mechanisms. Regardless, analysis of additional substrates should allow further correlation of functional specificity with protein kinase sequence for all protein kinases.

2. Protein Chip Technology

In addition to the rapid analysis of large number of samples, the protein chip technology described here has significant advantages over conventional methods. 1) The chip-based assays have high signal-to-noise ratios. We found that the signal-to-noise ratio exhibited using the protein chips is much better (>10 fold) than that observed for traditional microtiter dish assays (data not shown). Presumably this is due to the fact that $^{33}$P-γ-ATP does not bind the PDMS as much as microtiter dishes. 2) The amount of material needed is very small. Reactions volumes are ½₀-¼₀ the amount used in the 384-well microtiter dishes; less than 20 ng of protein kinase was used in each reaction. 3) The enzymatic assays using protein chips are extremely sensitive. Even though only 105 fusions were detectable by immunoblot analysis, 112 exhibited enzymatic activity greater than five-fold over background for at least one substrate. For example, Mps1 consistently exhibits the strongest activity in many of the kinase assays even though we have not been able to detect this fusion protein by immunoblot analysis (see FIGS. 1b and 3a). 4) Finally, the chips are inexpensive; the material costs less than eight cents for each array. The microfabricated molds are also easy to make and inexpensive.

In addition to the analysis of protein kinases, this protein chip technology is also applicable to a wide variety of additional assays, such as ATP and GTP binding assays, nuclease assays, helicase assays and protein-protein interaction assays. Recently, in an independent study, Phizicky and coworkers expressed yeast proteins as GST fusions under the much weaker CUP1 promotor[6]. Although the quality of their clones has not been established, they were able to identify biochemical activities using pools of yeast strains containing the fusion proteins. The advantage of our protein chip approach is that all samples can be analyzed in a single experiment. Furthermore, although this study used wells which have the advantage of segregating samples, flat PDMS chips and glass slides can also be used for different assays; these have the advantage that they can be used with standard pinning tool microarrayers. This technology can also be applied to facilitate hightroughput drug screening in which one can screen for compounds that inhibit or activate enzymatic activities of any gene products of interest. Since these assays will be carried out at the protein level, the results will be more direct and meaningful to the molecular function of the protein.

We configured the protein chip technology for a specific protein kinase assay using commonly available sample handling and recording equipment. For this purpose, array dimensions remained relatively large compared to dimensions readily available with microfabricated silicone elastomer structures[32]. We have cast PDMS structures with feature sizes two orders of magnitude smaller than those reported here using microlithographically fabricated molds, while others have reported submicron feature sizes in microfabricated structures[33]. These results indicate that well densities of microfabricated protein chips can be readily increased by several orders of magnitude. The protein chip technology reported here is readily scalable.

In conclusion, an inexpensive, disposable protein chip technology was developed for high throughput screening of protein biochemical activity. Utility was demonstrated through the analysis of 119 protein kinases from *Saccharomyces cerevisiae* assayed for phosphorylation of 17 different substrates. These protein chips permit the simultaneous measurement of hundreds of protein samples. The use of microfabricated arrays of wells as the basis of the chip technology allows array densities to be readily increased by several orders of magnitude. With the development of appropriate sample handling and measurement techniques, these protein chips can be adapted for the simultaneous assay of several thousand to millions of samples.

E. References

1. Fields, S., Kohara, Y., and Lockhart, D. J. Functional genomics. *Proc. Natl. Acad. Sci.* 96, 8825-26 (1999).
2. Goffeau, A., et al. Life with 6000 genes. *Science* 274, 563-567 (1996).
3. DeRisi, J. L., Iyer, V. R., and Brown, P. O. Exploring the metabolic and genetic control of gene expression on a genomic scale. *Science* 278, 680-686 (1997).
4. Winzeler, E. A., et al. Functional characterization of the *S. cerevisiae* genome by gene deletion and parallel analysis. *Science* 285, 901-906 (1999).
5. Heyman, J. A., et al. Genome-scale cloning and expression of individual open reading frames using topoisomerase I-mediated ligation. *Genome Res.* 9, 383-392 (1999).
6. Martzen, M. R., et al. A biochemical genomics approach for identifying genes by the activity of their products. *Science* 286, 1153-1155 (1999).
7. Plowman G. D., Sudarsanam S., Bingham J., Whyte D., and Hunter T. The protein kinases of *Caenorhabditis elegans*: A model for signal transduction in multicellular organisms. *Proc. Natl. Acad. Sci.* 96, 13603-12610 (1999).
8. Hunter, T., & Plowman, G. D. The protein kinases of budding yeast: six score and more. *TIBS* 22, 18-22 (1997).
9. Hudson, J. R., et al. The complete set of predicted genes from *Saccharomyces cerevisiae* in a readily usable form. *Genome Res.* 7, 1169-1173 (1997).
10. Mitchell, D. A., Marshall, T. K., and Deschenes, R. J. Vector for the inducible overexpression of glutathione S-transferase fusion protein in yeast. *Yeast* 9, 715-23 (1993).
11. Rogers, Y.-H., et al. Immobilization of oligonucleotides onto a glass support via disulfide bonds: a method for preparation of DNA microarrays. *Analy. Biochem.* 266, 23-30 (1999).
12. Stimpson, D. J., et al. Real-time detection of DNA hybridization and melting on oligonucleotide arrays by using optical wave guides. *Proc. Natl. Acad. Sci.* 92, 6379-6383 (1995).
13. Hunter, T. & Sefton, B. M. Protein phosphorylation. *Meth. in Enzym.* 200, 35-83 (1991).
14. Roemer, T. K., et al. Selection of axial growth sites in yeast requires Ax12p, a novel plasma membrane glycoprotein. *Genes & Dev.* 10, 777-793 (1996).
15. Weinert, T. A. & Hartwell, L. H. Cell cycle arrest of cdc mutants and specificity of the RAD9 checkpoint. *Genetics* 134, 63-80 (1993).
16. Jaquenoud, M., Gulli, M. P., Peter, K., and Peter, M. The Cdc42p effector Gic2p is targeted for ubiquitin-dependent degradation by the SCFGrr1 complex. *EMBO J.* 17, 5360-5373 (1998).
17. Menees, T. M., Ross-MacDonald, P. B., and Roeder, G. S. MEI4, a meiosis-specific yeast gene required for chromosome synapsis. *Mol. Cell Biol.* 12, 1340-1351 (1992).
18. Bailis, J. M., & Roeder, G. S. Synaptonemal complex morphogenesis and sisterchromatid cohesion require Mek1-dependent phosphorylation of a meiotic chromosomal protein. *Genes & Dev.* 12, 3551-3563 (1998).
19. Stern, D. F., Zheng, P., Beidler, D. R., and Zerillo, C. Spk1, a new kinase from *Saccharomyces cerevisiae* phosphorylates proteins on serine, threonine, and tyrosine. *Mol. Cell. Biol.* 11, 987-1001 (1991).
20. Kaouass, M., et al. The STK2 gene, which encodes a putative Ser/Thr protein kinase, is required for high-affinity spermidine transport in *Saccharomyces cerevisiae. Mol. Cell Biol.* 17, 2994-3004 (1997).
21. Barral, Y., Parra, M., Bidlingmaier, S., and Snyder, M. Niml-related kinases coordinate cell cycle progression with the organization of the peripheral cytoskeleton in yeast. *Genes & Dev.* 13, 176-187 (1999).
22. Madden, K., Sheu, Y.-J., Baetz, K., Andrews, B., and Snyder, M. SBF cell cycle regulator as a target of the yeast PKC-MAP kinase pathway. *Science* 275, 1781-1784 (1997).
23. Sobel, S. G. & Snyder, M. A highly divergent gamma-tubulin gene is essential for cell growth and proper microtubule organization in *Saccharomyces cerevisiae. J. Cell Biol.* 131, 1775-1788 (1995).
24. Ferrigno, P., Posas, F., Koepp, D., Saito, H., and Silver, P. A. Regulated nucleo/cytoplasmic exchange of HOGI MAPK requires the importin beta homologs NMD5 and XPO1. *EMBO J.* 17, 5606-5614 (1998).
25. Ho, U., Mason, S., Kobayashi, R., Heokstra, M., and Andrew, B. Role of the casein kinase I isoform, Hrr25, and the cell cycle-regulatory transcription factor, SBF, in the transcriptional response to DNA damage in *Saccharomyces cerevisiae. Proc. Natl. Acad. Sci.* 94, 581-586 (1997).
26. Wurgler-Murphy, S. M., Maeda, T., Witten, E. A., and Saito, H. Regulation of the *Saccharomyces cerevisiae* HOG1 mitogen-activated protein kinase by the PTP2 and PTP3 protein tyrosine phosphatases. *Mol. Cell Biol.* 17, 1289-1297 (1997).
27. Santos, T. & Hollingsworth, N. M. Redip, a MEK1-dependent phosphoprotein that physically interacts with Hop1p during meiosis in yeast. *J. Biol. Chem.* 274, 1783-1790 (1999).
28. Holly, S. P. & Blumer, K. J. PAK-family kinases regulate cell and actin polarization throughout the cell cycle of *Saccharomyces cerevisiae. J. Cell Biol.* 147, 845-856 (1999).
29. Richman, T. J., Sawyer, M. M., and Johnson, D. I. The Cdc42p GTPase is involved in a G2/M morphogenetic checkpoint regulating the apical-isotropic switch and nuclear division in yeast. *J. Biol. Chem.* 274, 16861-16870 (1999).
30. Malathi, K., Xiao, Y., and Mitchell, A. P. Catalytic roles of yeast GSK3beta/shaggy homolog Rim11p in meiotic activation. *Genetics* 153, 1145-1152 (1999).
31. Owen, D. J., Noble, M. E., Garman, E. F., Papageorgiou, A. C., and Johnson, L. N. Two structures of the catalytic domain of phosphorylase kinase: an active protein kinase complexed with substrate analogue and product. *Structure*, 3, 467-474 (1995).
32. Xia, Y. & Whitesides, G. M. *Angew. Chem. Int. Ed.* 37, 550-(1997).
33. Jackman, R. J., Duffy, D. C., Chemiavskaya, O., and Whitesides, G. M. Using elastomeric membranes as dry resists and for dry lift-off. *Langmuir,* 15, 2973-2984 (1999).
34. Mylin, L. M., Hofmann, K. J., Schultz, L. D., and Hopper, J. E. Regulated GAL4 expression cassette providing controllable and high-level output from high-copy galactose promoters in yeast. *Methods Enzymol.* 185, 297-308 (1990).
35. Higgins, D. G., Thompson, J. D., and Gibson, T. J. Using CLUSTAL for multiple sequence alignments. *Methods Enzymol.* 266, 383-402 (1996).
36. Gonnet, G. H., Cohen, M. A., and Benner, S. A. Exhaustive matching of the entire protein sequence database. *Science.* 256, 1443-1445 (1992).
37. Bairoch, A. & Apweiler, R. The SWISS-PROT protein sequence data bank and its supplement TrEMBL. *Nucleic Acids Res.* 27, 49-54 (1999).

38. Barker, W. C., et al. The PIR-International Protein Sequence Database. *Nucleic Acids Res.* 27(1), 39-43 (1999).
39. Benson, D. A., et al. GenBank. *Nucleic Acids Res.* 27, 12-17 (1999).
40. Lipman, D. J. & Pearson, W. R. Rapid and sensitive protein similarity searches. *Science.* 277, 1435-1441 (1985).
41. Pearson, W. R. & Lipman, D. J. Improved tools for biological sequence comparison. *Proc. Natl. Acad. Sci.* 85, 2444-2448 (1988).
42. Dayhoff, M. O., Schwartz, R. M., and Orcutt, B. C. A model of evolutionary change in proteins. In *Atlas of Protein Sequence and Structure*, M. O. Dayhoff, Ed. Washington, D.C.: National Biomedical Research Foundation. pp 345-352 (1978).
43. Hanks, S. K. & Hunter, T. Protein Kinases 6. The eukaryotic protein kinase superfamily: kinase (catalytic) domain structure and classification. *FASEB J.* 9, 576596 (1995).
44. Felsenstein, J. PHYLIP—Phylogeny Inference Package (Version 3.2). *Cladistics.* 5, 164-166 (1989).
45. Fitch, W. M. & Margoliash, E. Construction of phylogenetic trees. *Science.* 155, 279-284 (1967).

VII. EXAMPLE II

Analysis of Yeast Protein Kinase Activity Using Protein Chips

A. Introduction

The following example presents three protocols that, for illustration purposes only, provide different methods of using the protein chips of the present invention to assay for protein kinase activity.

1. Assay Methods for Protein Kinase Activity i. Autophosphorylation Activity (1) Protein chips were washed three times with 100% EtOH at room temperature. The chips were then coated with the linker GPTS (1% in 95% EtOH) at room temperature for one hour with shaking. After washing with 100% EtOH three times, the chips were dried at 130° C. for 1.5 hours under vacuum.

(2) GST::yeast protein kinases, one kinase species per well, were bound to the wells of the protein chip by incubation for at least one hour. The chip was further blocked by 1% BSA.

(3) Kinase buffer and a $^{33}$P-γ-ATP probe was added to each well, and incubated at 30° C. for 30 minutes. The chip was washed extensively after the phosphorylation reaction was completed.

(4) The specific $^{33}$P-γ-ATP signal, representing autophosphorylation, was detected and quantified by a phosphoimager.

ii. Kinase Activity—Protocol I (1) Protein chips were washed three times with 100% EtOH at room temperature. The chips were then coated with the linker GPTS (1% in 95% EtOH) at room temperature for one hour with shaking. After washing with 100% EtOH three times, the chips were dried at 130° C. for 1.5 hours under vacuum.

(2) A substrate (for example, GST::yeast protein) was bound to the chips by incubation for one or more hours. The chip was further blocked by 1% BSA, and the chip was washed.

(3) A different protein kinase was added to each well of the protein chip, along with kinase buffer and $^{33}$P-γ-ATP, and incubated at 30° C. for 30 minutes. The protein chip was washed extensively after the phosphorylation reaction was completed.

(4) The specific $^{33}$P-γ-ATP signal, representing phosphorylation of the substrate protein by the protein kinase probe, was detected and quantified by a phosphoimager.

iii. Kinase Activity—Protocol II (1) Protein chips were washed three times with 100% EtOH at room temperature. The chips were then coated with the linker GPTS (1% in 95% EtOH) at room temperature for one hour with shaking. After washing with 100% EtOH three times, the chips were dried at 130° C. for 1.5 hours under vacuum.

(2) A substrate (for example, GST::yeast protein) was bound to the chips by incubation for one or more hours. The chip was further blocked by 1% BSA and the chip was washed.

(3) A different protein kinase was added to each well of the protein chip, along with kinase buffer and P-γ-ATP, and incubated at 30° C. for 30 minutes. The protein chip was washed extensively after the phosphorylation reaction was completed. The chip was incubated with iodoacetyl-LC-biotin in the dark at room temperature overnight.

(4) After washing, the chip was probed with fluorescent-labeled avidin to detect the phosphorylation signals.

(5) The chip was then scanned using an Axon Genepix 4000A scanner, which was modified with a lens having an increased depth of focus of about 300-400 microns. The modifications allow scanning of surfaces mounted on a slide (e.g., the PDMS microarrays of the present invention), which would otherwise be out of the plane of focus. Using the modified Axon Genepix 4000A scanner, the arrays were scanned to acquire and quantify fluorescent signals.

VIII. EXAMPLE III

Analysis of Protein-Protein Interactions Using Protein Chips

A protein of interest ("probe protein") is recombinantly expressed in and purified from *E. coli* as a labeled fusion protein using standard protocols. The target proteins are attached to the wells of the chip, with a different target protein in each well. The purified probe protein is introduced into each well of the chip, and incubated for several hours or more. The chip is washed and probed with either: a) antibodies to the probe protein, or b) antibodies to the label on the fusion protein. The antibodies are labeled with a fluorescent label, such as Cy3 or Cy5, or are detected using a fluorescently labeled secondary antibody that detects the first antibody.

The following examples provide, for illustration purposes only, methods of using the protein chips of the present invention to assay for proteases, nucleases, or G-protein receptors. Protein-protein interactions generally can be assayed using the following or a similar method.

A. Analysis of Protease Activity

Protease activity is assayed in the following way. First, protein probes are prepared consisting of various combinations of amino acids, with a C-terminal or N-terminal mass spectroscopic label attached, with the only proviso being that the molecular weight of the label should be sufficiently large so that all labeled cleavage products of the protein can be detected. The protein probe is contacted with proteases attached to a protein chip at 37° C.

After incubation at 37° C. for an appropriate period of time, and washing with acetonitrile and trifluoroacetic acid, protease activity is measured by detecting the proteolytic products using mass spectrometry. This assay provides information regarding both the proteolytic activity and specificity of the proteases attached to the protein chip. Another rapid assay for protease activity analysis is to attach proteins of known sequence to the chip. The substrate proteins are fluorescently labeled at the end not attached to the chip. Upon incubation with the protease(s) of interest, the fluorescent label is lost upon proteolysis, such that decreases in fluorescence indicate the presence and extent of protease activity. This same type of assay can be carried out wherein the protein substrates are attached to beads placed in the wells of the chips.

B. Analysis of Nuclease Activity

Nuclease activity is assessed in the same manner as described for protease activity, above, except that nucleic acid probes/substrates are substituted for protein probes/substrates. As such, fluorescently tagged nucleic acid fragments that are released by nuclease activity can be detected by fluorescence, or the nucleic acid fragments can be detected directly by mass spectrometry.

C. Analysis of G-Protein Coupled Receptors

In another type of assay, compounds that bind G-protein coupled receptors are identified. Initially, the G-protein receptor is cloned as a GST fusion protein, with the GST portion attached to the C terminus of the G-protein because the C-terminus is generally not involved with determining probe specificity. The G-protein::GST fusion proteins are attached to the wells, preferably by association with glutathione. The G-protein receptors are then incubated with a mixture of compounds, such as a combinatorial chemical library or a peptide library. After washing, bound probes are eluted, for example by the addition of 25% acetonitrile/0.05% trichloroacetic acid. The eluted material is then be loaded into a MALDI mass spectrometer and the nature of the bound probes identified.

IX. EXAMPLE IV

Analysis of Protein Kinases Inhibition by Specific Inhibitors Using Protein Chips The following description provides, for exemplary purposes only, methods of using the protein chips of the present invention to examine protein kinases for sensitivity to protein kinase inhibitors. Protein-protein interactions generally can be assayed using the following or similar method.

Substrates were bound to the surface of the GPTS-treated microwells on the protein chip at room temperature for one hour, then blocked with 1% BSA and 100 mM Tris pH 7.5, and washed three times with TBS buffer. Kinases and different concentrations of kinase inhibitors were added to the microwells in the presence of $^{33}$P-γ-ATP. The phosphorylation reaction was carried out at 30° C. for thirty minutes. After completion of the reaction, the protein chip was washed extensively with TBS buffer at room temperature, and then allowed to dry. Phosphorylation signals were obtained by exposing the protein chip to either X-ray film or a phosphoimager.

A human protein kinase A (PKA), a human map kinase (MAPK), three yeast PKA homologs (TPK1, TPK2 and TPK3), and two other yeast protein kinases (HSL1 and RCK1) were tested against two substrates (i.e., a protein substrate for PKA and a commonly used kinase substrate, MBP) using different concentrations of PKIA (a specific human PKA inhibitor) or SB202190 (a MAPK inhibitor). As shown in FIG. 7, PKIα specifically inhibited PKA activities on both peptide and MBP substrates. However, PKIA did not inhibit the three yeast PKA homologs (TPK1, TPK2, TPK3) or the other two yeast protein kinases tested, HSL1 and RCK1). In addition, SB202190 did not inhibit PKA activity.

X. EXAMPLE V

Kinase Assays on a Glass Surface

1. Glass slides (Fisher, USA) were soaked in 28-30% ammonium hydroxide overnight at room temperature ("RT") with shaking.

2. The slides were rinsed with ultra-pure water four times for 5 minutes ("min") each, then rinsed with a large volume of 100% ethanol ("EtOH") to completely remove the water. Slides were then rinsed with 95% ethanol three times.

3. The slides were immersed in 1% 3-glycidoxypropyltrimethoxysilane (GPST) solution in 95% EtOH, 16 mM acetic acid ("HOAc") with shaking for 1 hr at room temperature. The slides were rinsed with 95% ethanol three times at RT.

4. The slides were cured at 135° C. for 2 hrs under vacuum. After cooling, the slides can be stored in Argon for months before use.

5. Approximately 10 μl of each protein substrate (in 40% glycerol) were arrayed onto a 96-well PCR plate on ice. A manual spotting device (V&P Scientific, USA) was used to spot approximately 3 nl of each of the samples onto the GPTS-treated glass slide at RT. In one embodiment, 768 samples are spotted on a single slide. The slides were incubated in a covered and clean chamber at RT for one hour.

6. A slide was blocked with 10 ml blocking buffer (100 mM glycine, 100 mM Tris, pH 8.0, 50 mM NaCl) at RT for one hour. The slides were washed with TBS buffer (50 mM Tris, pH 8.0, 150 mM NaCl) three times and spun to dryness at 1500 rpm for 5 mm.

7. The substrate surfaces on the slides were covered with the HybriWell Sealing System (Schleicher & Schuell, Germany) and 40 μl of kinase mixture, containing a protein kinase and $^{33}$P-γ-ATP as a labeling reagent, was added to the substrates on ice.

8. The reaction was incubated at 30° C. for 30 min in a humidity chamber. The seals were peeled from the slides, and the slides immersed into large volume of PBS buffer containing 50 mM EDTA. The slides were further washed with the same buffer 3×15 min at RT. The washed slides were then dried with Kimwipes.

9. To acquire the signals, the slides were exposed to a Phosphoimager screen and the data analyzed using ImageQuant software.

XI. References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A positionally addressable array comprising a plurality of different substances on a solid support, with each different substance being at a different position on the solid support, wherein the density of the different substances on the solid support is at least 100 different substances per cm², and wherein the plurality of different substances comprises at least 61 purified active kinases or functional kinase domains thereof of a mammal, that phosphorylates Serine/Threonine or tyrosine 61 purified active kinases or functional kinase domains thereof of a yeast, that phosphorylates Serine/Threonine or tyrosine or 61 purified active kinases or functional kinase domains thereof of a *Drosophila* that phosphorylates Serine/Threonine or tyrosine.

2. The array of claim 1 wherein the density of the different substances on the array is between 100 and 1,000 different substances per cm².

3. The array of claim 1 wherein the density of the different substances on the array is between 1,000 and 10,000 different substances per cm².

4. The array of claim 1 wherein the density of the different substances on the array is between 10,000 and 100,000 different substances per cm².

5. The array of claim 1 wherein the density of the different substances on the array is between 100,000 and 1,000,000 different substances per cm².

6. The array of claim 1 wherein the density of the different substances on the array is between 1,000,000 and 10,000,000 different substances per cm².

7. The array of claim 1 wherein the density of the different substances on the array is between 10,000,000 and 25,000,000 different substances per cm².

8. The array of claim 1 wherein the density of the different substances on the array is at least 25,000,000 different substances per cm².

9. The array of claim 1 wherein the density of the different substances on the array is at least 10,000,000,000 different substances per cm².

10. The array of claim 1 wherein the density of the different substances on the array is at least 10,000,000,000,000 different substances per cm².

11. The array of claim 1 wherein the solid support is a glass slide.

12. The array of claim 1 wherein the plurality of different substances are attached to the solid support via a 3-glycidoxypropyl-trimethoxysilane linker.

13. The array of claim 1 wherein the mammal is selected from the group consisting of human, primate, mouse, rat, cat, dog, horse, and cow.

14. The array of claim 13, wherein the organism is human.

15. The array of claim 13, wherein the organism is mouse.

16. The array of claim 13, wherein the organism is mouse.

17. The array of claim 13, wherein the organism is rat.

18. The positionally addressable protein array of claim 1, wherein the plurality of different substances comprises 61 different purified active kinases of an organism.

19. The positionally addressable protein array of claim 1, wherein the plurality of different substances comprises 92 different purified active kinases of a mammal, a yeast, or a *Drosophila*.

20. The positionally addressable protein array of claim 1, wherein the plurality of different substances comprises 110 different purified active kinases of a mammal, a yeast, or a *Drosophila*.

21. The positionally addressable protein array of claim 1, wherein the plurality of different substances comprises 116 different purified active kinases of a mammal, a yeast, or a *Drosophila*.

22. The positionally addressable protein array of claim 1, wherein the plurality of different substances comprises 119 different purified active kinases of a mammal, a yeast, or a *Drosophila*.

23. The positionally addressable protein array of claim 1, wherein the plurality of different substances comprises 122 purified active different kinases of a mammal, a yeast, or a *Drosophila*.

24. The positionally addressable array of claim 1, wherein the kinases are yeast kinases.

25. The positionally addressable array of claim 1, wherein the different substances are 61 purified active kinases.

26. The positionally addressable array of claim 25, wherein the kinases are serine/threonine kinase family members, tyrosine kinase family members, or serine/threonine kinase and tyrosine kinase family members.

27. The positionally addressable array of claim 1, wherein the functional kinase domains are functional kinase domains of serine/threonine kinase family members, functional kinase domains of tyrosine kinase family members, functional kinase domains of serine/threonine kinase family members or functional kinase domains of tyrosine kinase family members.

28. The positionally addressable array of claim 25, wherein the 61 purified active kinases are at least 100 amino acids in length.

* * * * *